(12) United States Patent
Wu et al.

(10) Patent No.: US 8,071,394 B2
(45) Date of Patent: Dec. 6, 2011

(54) TEST DEVICE FOR DETECTING AN ANALYTE IN A LIQUID SAMPLE

(75) Inventors: Xin Wu, Hangzhou (CN); Fei Gao, Hangzhou (CN); Jielin Dai, Hangzhou (CN); Yinfei Wu, Hangzhou (CN)

(73) Assignee: Alere Switzerland GmbH, Zug (CH)

( * ) Notice: Subject to any disclaimer, the term of this patent is extended or adjusted under 35 U.S.C. 154(b) by 285 days.

(21) Appl. No.: 12/360,087

(22) Filed: Jan. 26, 2009

(65) Prior Publication Data

US 2009/0232702 A1    Sep. 17, 2009

Related U.S. Application Data

(63) Continuation-in-part of application No. PCT/CN2007/070344, filed on Jul. 24, 2007.

(51) Int. Cl.
*G01N 33/53* (2006.01)
(52) U.S. Cl. .......... 436/518; 436/514; 435/283.1; 435/287.1; 435/287.2; 435/970; 422/401; 422/425; 422/430
(58) Field of Classification Search .......... 436/514, 436/518; 435/283.1, 287.1, 287.2, 970; 422/401, 422/425, 430
See application file for complete search history.

(56) References Cited

U.S. PATENT DOCUMENTS

| | | | |
|---|---|---|---|
| 3,896,974 A | 7/1975 | McIntosh | |
| 4,014,748 A | 3/1977 | Spinner et al. | |
| 4,114,605 A | 9/1978 | McGhee et al. | |
| 4,275,149 A | 6/1981 | Litman et al. | |
| 4,299,916 A | 11/1981 | Litman et al. | |
| 4,458,020 A | 7/1984 | Bohn et al. | |
| 4,635,488 A | 1/1987 | Kremer | |
| 4,768,238 A | 9/1988 | Kleinberg et al. | |
| 4,771,486 A | 9/1988 | Gutierrez et al. | |
| 4,817,632 A | 4/1989 | Schramm | |
| 4,853,325 A | 8/1989 | Vodian et al. | |
| 4,857,453 A | 8/1989 | Ullman et al. | |
| 4,877,850 A | 10/1989 | Geibel et al. | |
| 4,886,175 A | 12/1989 | Schlaudecker | |
| 4,923,798 A | 5/1990 | LeMoine et al. | |
| 4,955,745 A | 9/1990 | Vauquelin | |
| 4,962,025 A | 10/1990 | Moldowan | |
| 5,050,616 A | 9/1991 | Wolff et al. | |
| 5,073,484 A | 12/1991 | Swanson et al. | |
| 5,076,474 A | 12/1991 | Hansen | |
| 5,119,831 A | 6/1992 | Robin et al. | |
| 5,141,850 A * | 8/1992 | Cole et al. | 436/525 |

(Continued)

FOREIGN PATENT DOCUMENTS

CN        1084045 A        3/1994
(Continued)

OTHER PUBLICATIONS

U.S. Appl. No. 60/233,739, filed Sep. 19, 2000, Tung et al.
(Continued)

*Primary Examiner* — Bao Thuy L Nguyen
(74) *Attorney, Agent, or Firm* — DLA Piper LLP (US)

(57) ABSTRACT

The present invention relates to test devices, and in particular devices capable of detecting the presence or absence of an analyte in a sample, such as a liquid sample. Also provided are methods of using such devices for quantitative or qualitative measurement of one or more analytes in a liquid sample.

8 Claims, 8 Drawing Sheets

U.S. PATENT DOCUMENTS

| | | |
|---|---|---|
| 5,160,329 A | 11/1992 | Oxley |
| 5,170,799 A | 12/1992 | Nagase et al. |
| 5,185,127 A | 2/1993 | Vonk |
| 5,186,900 A | 2/1993 | Jensen et al. |
| 5,211,182 A | 5/1993 | Deutsch et al. |
| 5,234,001 A | 8/1993 | Goldstein et al. |
| 5,246,145 A | 9/1993 | Leoncavallo et al. |
| 5,252,496 A | 10/1993 | Kang et al. |
| 5,260,031 A | 11/1993 | Seymour |
| 5,261,572 A | 11/1993 | Strater |
| 5,275,785 A | 1/1994 | May et al. |
| 5,328,058 A | 7/1994 | Leoncavallo et al. |
| 5,334,502 A | 8/1994 | Sangha |
| 5,339,829 A | 8/1994 | Thieme et al. |
| 5,352,410 A | 10/1994 | Hansen et al. |
| 5,376,337 A | 12/1994 | Seymour |
| 5,380,492 A | 1/1995 | Seymour |
| 5,393,496 A | 2/1995 | Seymour |
| 5,415,994 A | 5/1995 | Imrich et al. |
| 5,416,000 A | 5/1995 | Allen et al. |
| 5,424,193 A | 6/1995 | Pronovost et al. |
| 5,479,937 A | 1/1996 | Thieme et al. |
| 5,494,646 A | 2/1996 | Seymour |
| 5,504,013 A | 4/1996 | Senior |
| 5,559,041 A | 9/1996 | Kang et al. |
| 5,573,009 A | 11/1996 | Thieme et al. |
| 5,573,099 A | 11/1996 | Church et al. |
| 5,602,040 A | 2/1997 | May et al. |
| 5,609,160 A | 3/1997 | Bahl et al. |
| 5,622,871 A | 4/1997 | May et al. |
| 5,654,162 A | 8/1997 | Guire et al. |
| 5,656,503 A | 8/1997 | May et al. |
| 5,679,535 A | 10/1997 | Joyce et al. |
| 5,686,315 A | 11/1997 | Pronovost et al. |
| 5,707,818 A * | 1/1998 | Chudzik et al. .............. 435/7.93 |
| 5,712,170 A | 1/1998 | Kouvonen et al. |
| 5,714,341 A | 2/1998 | Thieme et al. |
| 5,736,322 A | 4/1998 | Goldstein |
| 5,738,634 A | 4/1998 | Caillouette |
| 5,766,961 A | 6/1998 | Pawlak et al. |
| 5,770,460 A | 6/1998 | Pawlak et al. |
| 5,786,227 A | 7/1998 | Charlton |
| 5,786,228 A | 7/1998 | Charlton |
| 5,786,427 A | 7/1998 | Kijima et al. |
| 5,830,154 A | 11/1998 | Goldstein et al. |
| 5,830,410 A | 11/1998 | Thieme et al. |
| 5,877,028 A | 3/1999 | Chandler et al. |
| 5,910,122 A | 6/1999 | D'Angelo |
| 5,916,815 A | 6/1999 | Lappe |
| 5,922,283 A | 7/1999 | Hsu |
| 5,935,864 A | 8/1999 | Schramm et al. |
| 5,965,453 A | 10/1999 | Skiffington et al. |
| 5,965,458 A | 10/1999 | Kouvonen et al. |
| 5,968,746 A | 10/1999 | Schneider |
| 5,976,895 A | 11/1999 | Cipkowski |
| 5,981,293 A | 11/1999 | Charlton |
| 5,981,300 A | 11/1999 | Moll et al. |
| 5,986,895 A | 11/1999 | Stewart et al. |
| 6,022,326 A | 2/2000 | Tatum et al. |
| 6,046,058 A | 4/2000 | Sun |
| 6,102,872 A | 8/2000 | Doneen et al. |
| 6,136,610 A | 10/2000 | Polito et al. |
| 6,140,136 A | 10/2000 | Lee |
| 6,150,178 A | 11/2000 | Cesarczyk et al. |
| 6,180,395 B1 | 1/2001 | Skiffington et al. |
| 6,183,972 B1 | 2/2001 | Kuo et al. |
| 6,187,268 B1 | 2/2001 | Albarella et al. |
| 6,187,269 B1 | 2/2001 | Lancesseur et al. |
| 6,187,598 B1 | 2/2001 | May et al. |
| 6,194,221 B1 | 2/2001 | Rehg et al. |
| 6,194,224 B1 | 2/2001 | Good et al. |
| 6,221,678 B1 | 4/2001 | Chandler |
| 6,223,947 B1 | 5/2001 | Bernard |
| 6,228,660 B1 | 5/2001 | May et al. |
| 6,235,241 B1 | 5/2001 | Catt et al. |
| 6,241,689 B1 | 6/2001 | Chard et al. |
| 6,248,598 B1 | 6/2001 | Bogema |
| 6,271,046 B1 | 8/2001 | Chandler |
| 6,277,587 B1 | 8/2001 | Lamster |
| 6,277,646 B1 | 8/2001 | Guirguis et al. |
| 6,291,178 B1 | 9/2001 | Schneider |
| 6,297,020 B1 | 10/2001 | Brock |
| 6,303,081 B1 | 10/2001 | Mink et al. |
| 6,306,642 B1 | 10/2001 | Nelson et al. |
| 6,316,205 B1 | 11/2001 | Guan et al. |
| 6,338,969 B1 | 1/2002 | Shareef et al. |
| 6,352,862 B1 | 3/2002 | Davis et al. |
| 6,368,873 B1 | 4/2002 | Chang et al. |
| 6,372,513 B1 | 4/2002 | Nguyen et al. |
| 6,372,514 B1 | 4/2002 | Lee |
| 6,372,515 B1 | 4/2002 | Casterlin et al. |
| 6,372,516 B1 | 4/2002 | Sun |
| 6,375,896 B1 | 4/2002 | Wuske et al. |
| 6,375,897 B1 | 4/2002 | Bachand |
| 6,379,620 B1 | 4/2002 | Tydings et al. |
| 6,391,652 B2 | 5/2002 | Okada et al. |
| 6,403,383 B1 | 6/2002 | Casterlin et al. |
| 6,418,606 B1 | 7/2002 | Bachand |
| 6,423,550 B1 | 7/2002 | Jenkins et al. |
| 6,429,026 B1 | 8/2002 | Pettersson et al. |
| 6,440,087 B1 | 8/2002 | Sangha |
| 6,443,892 B1 | 9/2002 | Kidwell |
| 6,464,939 B1 | 10/2002 | Bachand et al. |
| 6,468,474 B2 | 10/2002 | Bachand et al. |
| 6,485,982 B1 | 11/2002 | Charlton |
| 6,489,172 B1 | 12/2002 | Bachand et al. |
| 6,506,612 B2 | 1/2003 | Kang et al. |
| 6,514,768 B1 | 2/2003 | Guire et al. |
| 6,514,769 B2 | 2/2003 | Lee |
| 6,528,323 B1 | 3/2003 | Thayer et al. |
| 6,537,823 B1 | 3/2003 | Smith |
| 6,548,019 B1 | 4/2003 | Lee et al. |
| 6,565,808 B2 | 5/2003 | Hudak et al. |
| 6,656,744 B2 | 12/2003 | Pronovost et al. |
| 6,669,908 B2 | 12/2003 | Weyker et al. |
| 6,673,630 B2 | 1/2004 | Albarella et al. |
| 6,730,268 B2 | 5/2004 | Lee et al. |
| 6,780,160 B2 | 8/2004 | Zhou et al. |
| 6,887,681 B2 | 5/2005 | DiCesare et al. |
| 6,979,576 B1 | 12/2005 | Cheng et al. |
| 7,048,693 B2 | 5/2006 | Zhou et al. |
| 7,114,403 B2 | 10/2006 | Wu et al. |
| 7,270,959 B2 | 9/2007 | Hudak |
| 7,300,633 B2 | 11/2007 | Hudak et al. |
| 7,354,614 B2 * | 4/2008 | Quinlan et al. ................ 426/514 |
| 7,393,697 B2 * | 7/2008 | Charlton ........................ 436/518 |
| 7,410,771 B2 * | 8/2008 | Tsang et al. .................... 435/7.1 |
| 7,481,977 B2 | 1/2009 | Percival et al. |
| 7,517,495 B2 | 4/2009 | Wu et al. |
| 7,682,801 B2 * | 3/2010 | Esfandiari ...................... 435/7.1 |
| 2001/0004532 A1 | 6/2001 | Chandler |
| 2001/0008614 A1 | 7/2001 | Aronowitz |
| 2001/0008774 A1 | 7/2001 | May et al. |
| 2001/0021536 A1 | 9/2001 | Lee |
| 2001/0023076 A1 | 9/2001 | Guan et al. |
| 2001/0023324 A1 | 9/2001 | Pronovost et al. |
| 2001/0041368 A1 | 11/2001 | May et al. |
| 2002/0001845 A1 | 1/2002 | Klaerner et al. |
| 2002/0004019 A1 | 1/2002 | Bachand et al. |
| 2002/0015663 A1 | 2/2002 | Goldstein et al. |
| 2002/0020713 A1 | 2/2002 | Kis et al. |
| 2002/0031840 A1 | 3/2002 | Albarella et al. |
| 2002/0031845 A1 | 3/2002 | Cipkowski |
| 2002/0052050 A1 | 5/2002 | Douglas et al. |
| 2002/0085953 A1 | 7/2002 | Parker |
| 2002/0085958 A1 | 7/2002 | Nemcek et al. |
| 2002/0098512 A1 | 7/2002 | Goodell et al. |
| 2002/0132267 A1 | 9/2002 | Wong |
| 2002/0132370 A1 | 9/2002 | Lassen et al. |
| 2002/0137231 A1 | 9/2002 | Cipkowski |
| 2002/0146346 A1 | 10/2002 | Konecke |
| 2002/0150884 A1 | 10/2002 | Zmuda et al. |
| 2002/0155028 A1 | 10/2002 | Wong |
| 2002/0155029 A1 | 10/2002 | Mink et al. |
| 2002/0173047 A1 | 11/2002 | Hudak et al. |
| 2002/0192839 A1 | 12/2002 | Mink et al. |
| 2003/0045003 A1 | 3/2003 | Smith |

| | | | |
|---|---|---|---|
| 2003/0064526 A1 | 4/2003 | Niedbala et al. | |
| 2003/0129088 A1 | 7/2003 | Lee et al. | |
| 2003/0129673 A1 | 7/2003 | Schwarz et al. | |
| 2003/0138971 A1 | 7/2003 | D'Aurora | |
| 2003/0175992 A1 | 9/2003 | Toranto et al. | |
| 2003/0175993 A1 | 9/2003 | Toranto et al. | |
| 2003/0190259 A1 | 10/2003 | Alley | |
| 2003/0207466 A1 | 11/2003 | Po Lee | |
| 2004/0018636 A1 | 1/2004 | Zhou et al. | |
| 2004/0082878 A1 | 4/2004 | Baldwin et al. | |
| 2004/0184954 A1 | 9/2004 | Guo et al. | |
| 2004/0191760 A1 | 9/2004 | Zhou et al. | |
| 2005/0119589 A1 | 6/2005 | Tung et al. | |
| 2005/0180882 A1 | 8/2005 | Tung et al. | |
| 2005/0202568 A1 | 9/2005 | Tung et al. | |
| 2006/0034728 A1 | 2/2006 | Kloepfer et al. | |
| 2006/0121548 A1 | 6/2006 | Robbins et al. | |
| 2006/0292035 A1 | 12/2006 | Gould et al. | |
| 2007/0128070 A1 | 6/2007 | Wu et al. | |
| 2009/0117665 A1 | 5/2009 | Tung et al. | |
| 2009/0226883 A1 | 9/2009 | Wu et al. | |
| 2009/0232702 A1 | 9/2009 | Wu et al. | |

FOREIGN PATENT DOCUMENTS

| | | | |
|---|---|---|---|
| CN | 1314593 A | 9/2001 | |
| CN | 2476023 Y | 2/2002 | |
| CN | 1603823 A | 4/2005 | |
| CN | 1614383 A | 5/2005 | |
| CN | 1645146 A | 7/2005 | |
| EP | 0 390 984 A1 | 10/1990 | |
| EP | 0 392 096 A1 | 10/1990 | |
| EP | 0 455 916 A2 | 11/1991 | |
| EP | 0 455 916 A3 | 11/1991 | |
| EP | 0 500 172 A1 | 8/1992 | |
| EP | 0 542 107 A1 | 5/1993 | |
| EP | 0 561 322 A1 | 9/1993 | |
| EP | 0 455 916 B1 | 2/1996 | |
| EP | 0 734 684 A1 | 10/1996 | |
| EP | 0 734 685 A1 | 10/1996 | |
| EP | 0 734 686 A1 | 10/1996 | |
| EP | 0 753 148 B1 | 12/1998 | |
| EP | 1 216 931 A1 | 6/2002 | |
| EP | 1 275 962 A1 | 1/2003 | |
| EP | 1348960 A1 | 10/2003 | |
| GB | 855916 | 12/1960 | |
| JP | 11-304800 A | 11/1999 | |
| WO | WO 92/16842 A1 | 10/1992 | |
| WO | WO 93/11434 A1 | 6/1993 | |
| WO | WO 94/07419 A1 | 4/1994 | |
| WO | WO 94/18892 A1 | 9/1994 | |
| WO | WO 95/02822 A1 | 1/1995 | |
| WO | WO 95/07223 A2 | 3/1995 | |
| WO | WO 95/07223 A3 | 5/1995 | |
| WO | WO 95/27205 A1 | 10/1995 | |
| WO | WO 97/20502 A1 | 6/1997 | |
| WO | WO 98/44158 A1 | 10/1998 | |
| WO | WO 99/06827 A2 | 2/1999 | |
| WO | WO 99/06827 A3 | 4/1999 | |
| WO | WO 99/22639 A1 | 5/1999 | |
| WO | WO 99/22645 A1 | 5/1999 | |
| WO | WO 99/27139 A1 | 6/1999 | |
| WO | WO 99/50656 A1 | 10/1999 | |
| WO | WO 00/15020 A1 | 3/2000 | |
| WO | WO 00/20862 A1 | 4/2000 | |
| WO | WO 00/25666 A1 | 5/2000 | |
| WO | WO 00/64334 A1 | 11/2000 | |
| WO | WO 01/08993 A1 | 2/2001 | |
| WO | WO 01/81915 A1 | 11/2001 | |
| WO | WO 01/49820 A1 | 12/2001 | |
| WO | WO 02/04941 A2 | 1/2002 | |
| WO | WO 02/07645 A2 | 1/2002 | |
| WO | WO 02/04942 A1 | 2/2002 | |
| WO | WO 02/16946 A2 | 2/2002 | |
| WO | WO 02/04941 A3 | 4/2002 | |
| WO | WO 02/07645 A3 | 5/2002 | |
| WO | WO 02/058600 A2 | 8/2002 | |
| WO | WO 02/059600 A2 | 8/2002 | |
| WO | WO 02/082040 A2 | 10/2002 | |
| WO | WO 02/096480 A2 | 12/2002 | |
| WO | WO 02/16946 A3 | 1/2003 | |
| WO | WO 02/082040 A3 | 1/2003 | |
| WO | WO 02/059600 A3 | 3/2003 | |
| WO | WO 02/96480 A3 | 3/2003 | |
| WO | WO 02/58600 A3 | 3/2004 | |
| WO | WO 2005/008216 A2 | 1/2005 | |
| WO | WO 2005/050165 A2 | 6/2005 | |
| WO | WO 2005/008216 A3 | 7/2005 | |
| WO | WO 2005/050165 A3 | 7/2005 | |
| WO | WO 2007/062575 A1 | 6/2007 | |
| WO | WO 2008/012566 A2 | 1/2008 | |
| WO | WO 2008/012566 A3 | 11/2008 | |

OTHER PUBLICATIONS

International search report dated Jul. 19, 2006 for PCT Application No. US2004/038427.

International search report dated Feb. 1, 2007 for PCT Application No. CN2006/003028.

International search report dated Nov. 1, 2007 for PCT Application No. CN2007/70344.

International search report dated Mar. 16, 2009 for PCT Application No. IB2008/001831.

* cited by examiner

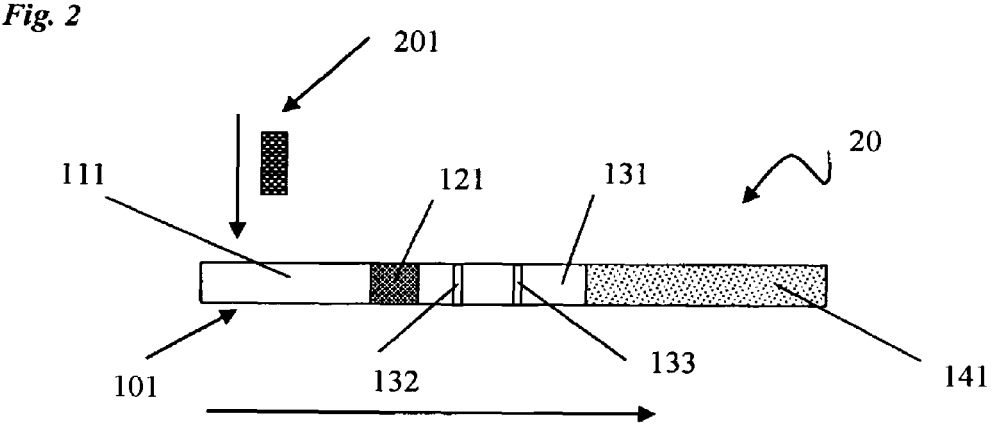
Fig. 2
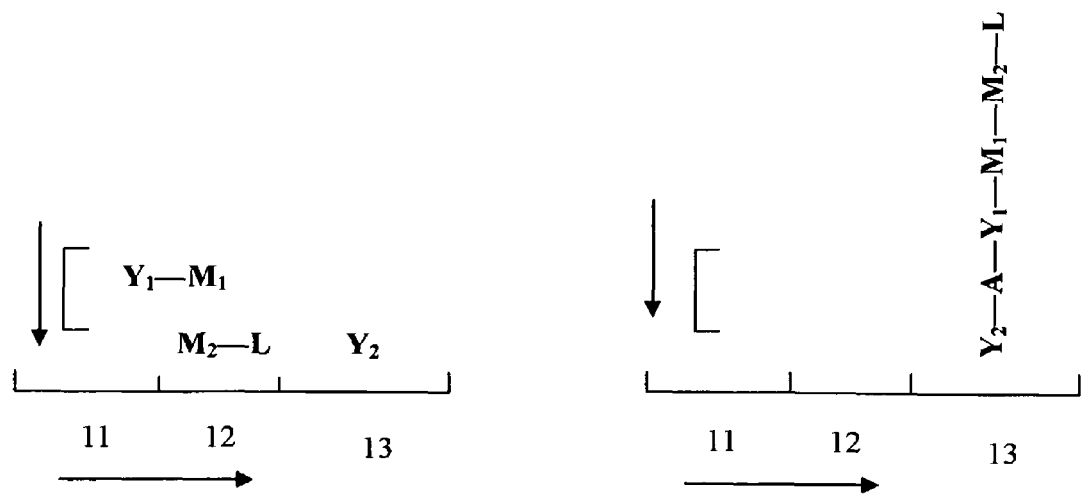
Fig. 3A
Fig. 3B

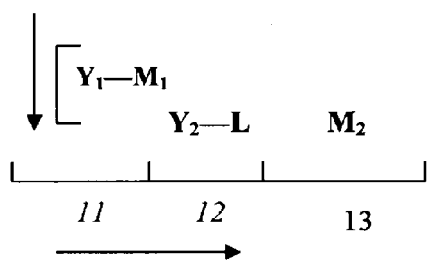
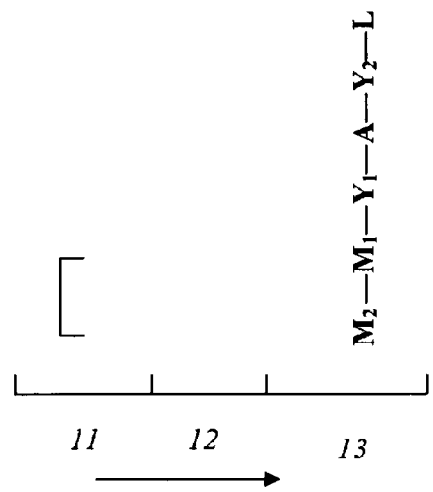
Fig. 4A
Fig. 4B
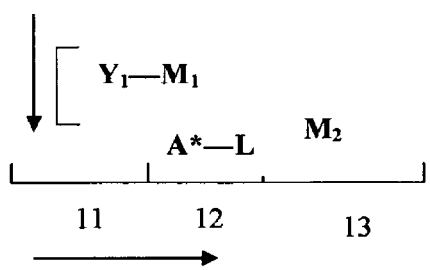
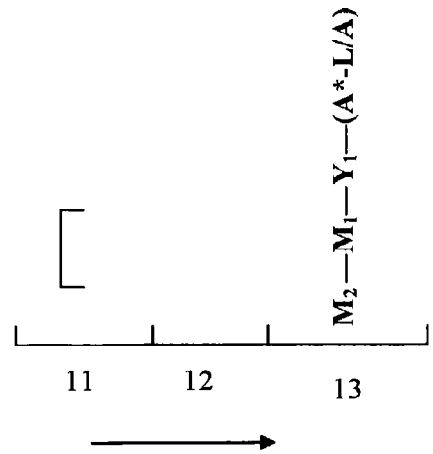
Fig. 5A
Fig. 5B

TEST DEVICE FOR DETECTING AN ANALYTE IN A LIQUID SAMPLE

RELATED APPLICATIONS

This application is a continuation-in-part of International PCT Application No. PCT/CN2007/070344, with an international filing date of Jul. 24, 2007, which in turn claims priority to CN Application No. CN 200610052628.1, filed Jul. 26, 2006 and CN 200620106025.0, filed Jul. 26, 2006, all of which are incorporated herein by reference in their entirety.

FIELD OF THE INVENTION

The present invention is directed to devices and methods for the detection of an analyte in a liquid sample.

BACKGROUND

Lateral flow devices have been described and utilized for detecting analyte(s) present in a test sample. An exemplary conventional lateral flow device is illustrated in FIG. 1C. The lateral flow test device 10 typically includes a reagent zone and a test zone 13. The reagent zone includes a sample receiving zone 11 and a label zone 12. The test zone 13 can contain a test result zone 132 and a control test result zone 133 located downstream of the test result zone 132. Typically, the sample receiving zone contains a porous sample receiving pad 111 and the label zone contains a conjugate pad 121, both of which constitute the reagent zone where all necessary assay reagents are contained therein. The test zone is typically in form of a test strip 131 with a test result zone 132 and a control test result zone 133 located downstream. A calorimetric readout appearing in the test result zone typically indicates the presence of the analyte being tested. The lateral flow device typically contains an absorbent pad 141, which is in fluid communication with the elements 11, 121, and 131 along the direction indicated by the arrow of FIG. 1C. Conventional lateral device are made of nitrocellulose strip or nylon which are immobilized with binding agents that bind the analyte being tested. See, for example, the lateral flow test devices described in U.S. Pat. Nos. 4,857,453; 5,073,484; 5,119,831; 5,185,127; 5,275,785; 5,416,000; 5,504,013; 5,602,040; 5,622,871; 654,162; 5,656,503; 5,686,315; 5,766,961; 5,770,460; 5,916,815; 5,976,895; 6,248,598; 6,140,136; 6,187,269; 6,187,598; 6,228,660; 6,235,241; 6,306,642; 6,352,862; 6,372,515; 6,379,620 and 6,403,383, each incorporated herein by reference in their entirety.

Either competitive or non-competitive assays can be performed with the conventional lateral flow test devices for detecting the presence of an analyte in a liquid sample. However, such devices and methods are not particularly amenable to adjusting detection thresholds, which allow for a positive or negative signal to be produced at a predetermined analyte concentration. In addition, these devices and methods are not particularly useful for measuring analytes at low concentrations with high degree of accuracy. When an analyte is present at very low concentration in a liquid sample, a buffer solution is required to extract the analyte from the sample, which can affect the result and create inconvenience and raise safety concerns to the person who is handling the assay. Therefore, there exists a need for testing devices that require minimum manual operation while ensuring accurate and reliable test results.

SUMMARY OF THE INVENTION

The invention provides for a device for determining the presence of an analyte in a liquid sample, comprising: a test strip comprising a first reagent zone located upstream of a test result zone; a second reagent zone separable from and located upstream to the first reagent zone, wherein the second reagent zone comprises a mobilizable analyte-binding moiety which exhibits specific binding to a first reagent that is disposed in dry state in said test strip. The device can be configured to provide a fluidic flowpath when said second reagent zone is placed in fluidic communication with the test strip. The test device can have a flow path along which the liquid sample flows into the second reagent zone to mobilize the analyte-binding moiety and to effect formation of an analyte:analyte-binding moiety complex in a mixture for a sufficient amount of time required for said formation. Additionally, along said flowpath, the mixture can flow into the first reagent zone and the test result zone to react with at least two other specific binding moieties such that a detectable complex indicative of the presence of said analyte:analyte-binding moiety complex is formed. In some embodiments, the second reagent zone contained in a subject device is separable from the first reagent zone via an adjustable liquid passage that blocks or permits fluidic communication between the second reagent zone and the first reagent zone.

In a related but separate embodiment, the invention provides for a test device for detecting the presence of an analyte in a liquid sample, comprising: (a) a test compartment comprising at least one test strip, said test strip comprising a first reagent zone and a test result zone, disposed thereon in dry state reagents necessary for forming a detectable complex indicative of the presence of said analyte; and (b) a sample collection well comprising a second reagent zone, wherein the second reagent zone comprises a mobilizable analyte-binding moiety which exhibits specific binding to said reagents disposed in said test strip; and wherein the test device having a first position prohibiting fluidic communication between the test strip and the sample collection well, and a second position permitting fluidic communication between the test strip and the sample collection well. The sample collection well can be configured to permit contact of the liquid sample with the second reagent zone prior to allowing fluidic communication between the sample collection well and the test strip via switching from the first position to the second position. In some embodiments of the invention, the sample collection well is configured to accept a sample collector comprising an absorbent.

In some embodiments, the analyte-binding moiety contained in the second reagent zone can comprise one member of a binding pair, wherein said one member is capable of specific binding to the other member of said pair, said other member being conjugated to a label.

In some embodiments, the analyte-binding moiety contained in the second reagent zone can comprise one member of a binding pair, wherein said one member is capable of specific binding to the other member of said pair, said other member being immobilized to the test result zone.

The first reagent zone can comprise an analyte mimic that is conjugated to a label, wherein said mimic competes with the analyte for binding to the analyte-binding moiety.

In some embodiments, the analyte-binding moiety contained in the second reagent zone comprises one member of a binding pair (Y1-M1), and the first reagent zone comprises the other member of the binding pair conjugated to a label (M2-L), and the test result zone comprises an analyte-binding moiety distinct from the one contained in the second reagent zone (Y2), and wherein upon flowing said liquid sample along said flowpath, at least two specific binding events occur on said test strip to yield the detectable complex of Y2: analyte: Y1-M1:M2-L as shown in FIG. 3B.

In other embodiments of the invention, the analyte-binding moiety contained in the second reagent zone comprises one member of a binding pair (Y1-M1), and the first reagent zone comprises a distinct analyte-binding moiety different from the one contained in the second reagent zone, said distinct analyte-binding moiety being conjugated to a label (Y2-L), and wherein the test result zone comprises the other member of said binding pair (M2), and wherein upon flowing said liquid sample along said flowpath, at least two specific binding events occur on said test strip to yield the detectable complex of M2:M1-Y1 analyte: Y2-L as shown in FIG. 4B.

The analyte-binding moiety contained in the second reagent zone can comprise one member of a binding pair (Y1-M1), and wherein the first reagent zone comprises an analyte mimic that is conjugated to a label (A*-L), said mimic competing with the analyte for binding to the analyte-binding moiety, and wherein the test result zone comprises the other member of said binding pair (M2), and wherein upon flowing said liquid sample along said flowpath, at least two specific binding events occur on said test strip to yield the detectable complex of M2:M1-Y1:A*-L as shown in FIG. 5B.

The analyte-binding moiety can comprise an antibody. The analyte can comprises a drug abuse chemical. The drug abuse chemical includes but is not limited to THC and BZO. The members of the binding pair can lack specific binding to said analyte.

The at least two specific binding moieties can be members of a binding pair selected from the group consisting of biotin/avidin, biotin/streptavidin, and mouse IgG/anti-mouse IgG. The detectable complex comprises a label, said label being a color particle or a water-soluble dye.

The device can comprise a housing with the first reagent zone and the detection zone therein and a liquid sample container comprising the second regent therein; and wherein the house and the liquid sample are in fluid communication.

The invention provides for a method for detecting the presence of an analyte in a liquid sample comprising: allowing the liquid sample applied to the second reagent zone of the subject device to flow into the first reagent zone under conditions such that a detectable complex indicative of the presence of said analyte:analyte-binding moiety complex is formed, thereby detecting the presence of the analyte.

Prior to placing said second reagent zone in fluidic communication with the test strip, the liquid sample can be in contact with the second reagent zone for a period of time sufficient to effect formation of said analyte:analyte-binding moiety complex. The period of time can be from at least about 1 to about 30 minutes.

The invention also provides for a method for detecting the presence of an analyte in a liquid sample comprising: applying the liquid sample to the sample collection well of the subject device to effect formation of an analyte:analyte-binding moiety complex in a mixture in the second reagent zone; and switching the sample collection well from the first position to the second position to permit flow of said mixture to the test strip to permit formation of a detectable complex indicative of the presence of said analyte:analyte-binding moiety complex, thereby detecting the presence of the analyte.

Prior to placing said second reagent zone in fluidic communication with the test strip via switching from the first position to the second position, the liquid sample can be in contact with the second reagent zone for a period of time sufficient to effect formation of said analyte:analyte-binding moiety complex. The period of time can be from at least about 1 to about 30 minutes.

The first reagent zone can be located on a first porous membrane. The second reagent zone can be located on a second porous membrane that is separated from the first porous membrane.

The present invention relates to test devices. A test device provided by the present invention includes a test element and a second reagent zone that can be separated from but also be in fluidic communication with the test element; wherein the test element includes a first reagent zone and a test zone. When using the test device, a liquid sample that is first applied to the second reagent zone flows to the first reagent zone and then to the test result zone. Using the test device not only increases the accuracy and/or sensitivity of the test, but avoids adding additional buffer solution into the liquid sample prior to applying the sample to the test device. An example of such buffer would be a buffer for extracting a small chemical from a liquid sample.

In one aspect of the present invention, a test device provided for detecting an analyte in a liquid sample comprises (1) a test element comprising a first reagent zone that is in fluid communication with a downstream test result zone, whereon an analyte-binding moiety is immobilized and; (2) a second reagent zone with a mobilizable dried binding moiety exhibiting for specific binding to the analyte, wherein the second reagent zone is in fluid communication with the test element and can be separate from the test element. When using the test device, the liquid sample is applied to the second reagent zone to form a liquid mixture and then allowed to flow to the detection zone of the test element, where a test result on the detection zone can be detected. Utilizing the devices and methods of the present invention can result in high detection sensitivity. In some embodiments, additional extraction solution or buffer solution is not added to the liquid sample prior to applying the liquid sample to the test device and/or after applying the liquid sample to the test device.

In some other embodiments, the devices and methods of the invention can be used to determine the presence or absence of an analyte in a sample using non-competitive binding. For example, the second zone can have a first analyte-binding moiety (Y1) that exhibits specific binding to a target analyte (A), wherein the first mobilizable molecule can be conjugated with a first member (M1) of a binding pair (M1/M2) which is unrelated to the analyte; the first reagent zone can include a label zone with a detectable label (L) conjugated to a second analyte-binding moiety (Y2) that exhibits specific binding to the target analyte; the detection zone can include a second member (M2) of the binding pair. See e.g., FIG. 4A-4B. Y2 can be a binding moiety that is distinct from Y1. Y1 and Y2 can both bind to the analyte. The first member of the binding pair (M1) can bind to the second member of the binding pair (M2). When using the device, a liquid sample can be applied to the second reagent zone of the test device. If a target analyte is present in the liquid sample, the first analyte-binding moiety can bind the target analyte and form a complex (M1-Y1:A) that can be mobilized by the fluid sample from the second reagent zone into the label zone of the first reagent zone of the test element where a new complex is formed (M1-Y1:A:Y2-L). The new complex can reach to the detection zone where the detectable label can be captured by the second member of the binding pair (M2) to indicate that a target analyte is present in the liquid sample (a positive result) and form a detectable complex. In preferred embodiments, the first reagent zone has a sample receiving zone that can be in fluidic communication with the label zone. The first reagent zone can receive the sample from the second reagent zone. If no target analyte present in the liquid sample, no detectable label is captured on the detection zone and a negative result is shown.

Alternatively, the second zone can comprise a first analyte-binding moiety (Y1) that exhibits specific binding to a target analyte (A), wherein the first mobilizable molecule can be conjugated with a first member (M1) of a binding pair (M1/M2) which is unrelated to the analyte; the first reagent zone can comprise a label zone with a detectable label (L) conjugated to the other member of a binding pair (M2); the detection zone can comprise e a second analyte-binding moiety (Y2). See e.g., FIG. 3A-3B. Y2 can be a binding moiety that is distinct from Y1. Y1 and Y2 can both bind to the analyte. The first member of the binding pair (M1) can bind to the second member of the binding pair (M2). When using the device, a liquid sample can be applied to the second reagent zone of the test device. If a target analyte is present in the liquid sample, the first analyte-binding moiety can bind the target analyte and form a complex (M1-Y1:A) that can be mobilized by the fluid sample from the second reagent zone into the label zone of the first reagent zone of the test element where a new complex is formed (A:Y1-M1: M2-L). The new complex can reach to the detection zone where the detectable label can be captured by the second analyte-binding moiety (Y2) to indicate that a target analyte is present in the liquid sample (a positive result) and form a detectable complex. In preferred embodiments, the first reagent zone has a sample receiving zone that can be in fluidic communication with the label zone. The first reagent zone can receive the sample from the second reagent zone. If no target analyte present in the liquid sample, no detectable label is captured on the detection zone and a negative result is shown. See, e.g., FIG. 3A-3B.

The terms A, Y1, Y2, M1 and M2 are only used as to facilitate understanding of the present invention and do not limit the scope of the present invention. The dashes can represent covalent interactions, or otherwise pre-formed bonds or binding. The colons can represent binding interactions or binding events that occur between components. The binding events can be high-affinity or specific binding events.

In other embodiments, when the analyte is an antibody, a first antigen having specific binding to the antibody is conjugated with a first member of a binding pair that is not relevant to the antibody. The antigen conjugated to the first member can be movably dried on the second reagent zone; a color label conjugated with a second antigen or binding moiety, exhibiting specific binding to the antibody, is movably dried on the label zone; and a second member of the binding pair is immobilized on the test result zone. In another embodiment, when the analyte is an antigen, a first antibody, conjugated with a first member of a binding pair that is not relevant to the antibody, but capable of specific binding to the antigen, is movable dried on the second reagent zone; a color label conjugated with a second antibody specific binding to the antigen is movable dried on the label zone; a second member of the binding pair is immobilized on the test result zone. If the test sample contains the analyte being tested, the test zone can change color indicating a positive result. By contrast, there will be no color change if the analyte is absent and hence the result is negative.

Utilizing a competitive binding assay, in some embodiments, an analyte-binding moiety (Y1) for a target analyte is movably dried on the second reagent zone, wherein the analyte-binding moiety Y1 is conjugated with a first member M1 of a binding pair (M1/M2) that are not related to the target analyte; the label zone includes a detectable label (L) conjugated with an analyte mimic (A*) that can be moved by the liquid sample; and the second member M2 of the binding pair is immobilized on the test result zone. When using the test device, a liquid sample is applied to the test device as to contact to the second reagent zone first. If a target analyte is present in the liquid sample, then the analyte can be bound by the analyte-binding moiety as to form a complex (A:Y1-M1) that can be moved by the liquid flow to the label zone, which has element L-A*, and then the mixture, including the complex (A:Y1-M1), detectable label and the analyte mimic (L-A*), can be moved by the liquid sample to reach to the detection zone where a detectable label may not be captured. A negative result is detected on the test result zone. At the label zone, the complex (A:Y1-M1) can dissociate by competition with the labeled analyte mimic to form A+Y1-M1+ L-A* and then A+L-A*:Y1-M1. The liquid sample containing the complexes flow to the test result zone, where the immobilized member (M2) on the test result zone captures the complexes by binding to M1 of the complex, allowing for determination of the test result. If no detectable label is captured at the test result zone, a positive result is detected, which indicates the presence of the analyte of interest in the sample. Conversely, a negative result indicates the absence of the analyte of interest in the sample. See, e.g. FIG. 5A-5B.

In some preferred embodiments, the molecule dried on the second reagent zone is an antibody exhibiting specific binding to a target analyte, wherein the antibody is conjugated to a biotin molecule; the label zone of the test elements has a detectable label and an analyte mimic; and a streptavidin is immobilized on the test result zone.

In other embodiments, a test device is provided for detecting an analyte in a liquid sample comprising (1) a test element including a first reagent zone that is in fluid communication with a detection zone, whereon an analyte-binding moiety is immobilized and; (2) a second reagent zone, in fluid communication with the test element and that is separate from the test element, where the second reagent zone has a moveably dried molecule exhibiting specific binding to an analyte; and wherein the second reagent zone can be contacted in a sample collection well that is a part of and in fluidic communication with a casing that also houses said test element. When detecting a target analyte in a liquid sample; the liquid sample is applied to the collection well as to contact to the second reagent zone first, then the liquid sample is moved to the test element contained within the casing. In a preferred embodiment, an analyte-binding moiety (Y1) having binding to the target analyte is movably dried on the second reagent zone, wherein the molecule Y1 is conjugated to a first member M1 of a binding pair (M1/M2), where M1 and M2 are not related to the target analyte and do not have specific binding to the target analyte; the label zone includes a detectable label (L) and an analyte mimic (A*) that can be moved by the liquid sample; and the second member M2 of the binding pair is immobilized on the test result zone.

Another aspect of the invention provides for a method for detecting an analyte in a liquid sample comprising providing a test device comprising a second reagent zone with a moveably dried molecule exhibiting specific binding to the analyte, where the second reagent zone is in fluid communication with a test element that comprises a first reagent zone, which is in fluid communication with a detection zone. The first reagent zone can comprise a label zone with a dried label. An analyte-binding moiety can be immobilized on the test result zone. The methods of the invention also provide for applying a liquid sample onto the second reagent zone, moving the liquid sample from the first reagent zone to the test result zone, and determining the test result based on the test result zone.

In another aspect of this present invention, a test kit is provided. The test kit includes a test device described above and a sample collector, the test device comprising a second reagent zone with a moveably dried molecule exhibiting specific binding to an analyte, where the reagent zone is in fluid communication with a test element that comprises a first reagent zone that is in fluid communication with a detection zone. The first reagent zone can comprise a label zone with a dried label and the rest result zone comprising an analyte-binding moiety that is immobilized. The second reagent zone can be separate from the test element.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

FIG. 2 is a perspective view of a test device.

FIG. 3A is an illustration of an embodiment of present invention before a liquid sample is applied to the second reagent zone.

FIG. 3B is an illustration of an embodiment of present invention showing a test result on the test result zone 13 after a liquid sample is applied to the second reagent zone if an analyte is present in the liquid sample.

FIG. 4A is an illustration of an embodiment of the present invention showing a test device before a liquid sample is applied to the second reagent zone.

FIG. 4B is an illustration of an embodiment of present invention showing a test result on the test result zone 13 after a liquid sample is applied to the test device if an analyte is present in the liquid sample.

FIG. 5A is an illustration of a test device.

FIG. 5B is an illustration of the test device showing a test result on the test result zone after a liquid sample is applied to the second reagent zone of the test device, when an analyte is present in the liquid sample.

DETAILED DESCRIPTION

Figure 1A:
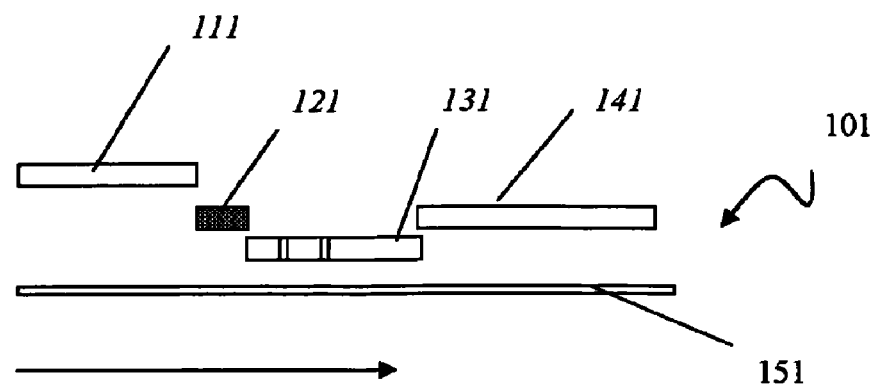
FIG. 1A is a perspective view of a lateral flow device including a sample receiving pad 111, a label pad 121, test strip 131 and an absorbent pad 131 that are arranged on the back pad 151 in this order of the direction of the liquid flow.
Figure 1B:
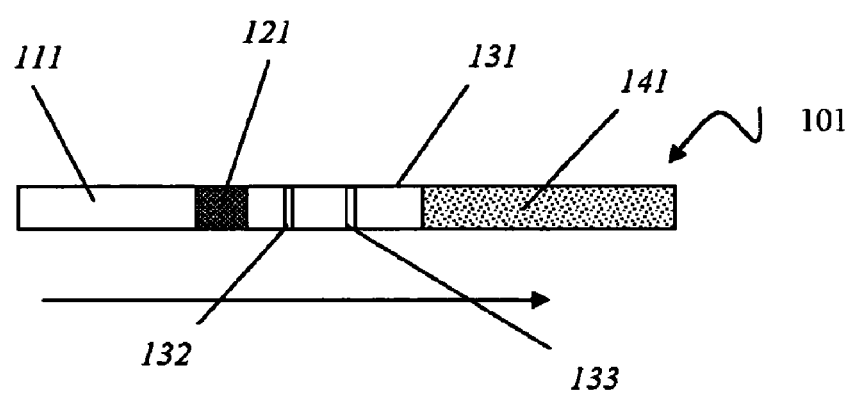
FIG. 1B is a top view of a lateral flow device showing a test result zone 132 and a result control zone 131 on the test strip 131.

The present invention relates to a test device, such as test for determining drugs of abuse in biological samples. As used in the specification and claims, the singular forms "a", "an" and "the" include plural references unless the context clearly dictates otherwise. The test device of the present invention includes a test element and a second reagent zone that is separate from and in fluidic communication with the test element; wherein the test element includes a first reagent zone and a test result zone. When using the test device, a liquid sample can be applied to the second reagent zone, then flow to the first reagent zone, and then the test result zone.

Unless defined otherwise, all technical and scientific terms used herein have the same meaning as commonly understood by one of ordinary skill in the art to which this invention belongs.

"Assaying" denotes testing for or detecting the presence of a substance or material, such as, but not limited to, a chemical, an organic compound, an inorganic compound, a metabolic product, a drug or a drug metabolite, an organism or a metabolite of such an organism, a nucleic acid, a protein, or a combination thereof. Optionally, assaying denotes measuring the amount of the substance or material. Assaying further denotes an immunological test, a chemical test, an enzymatic test, and the like.

"Sample" or "specimen" may be used interchangeably. "Sample" or "specimen" denotes any material to be assayed for the presence and/or concentration of an analyte in a sample or specimen, or to determine the presence and/or numbers of one or more components of a sample or specimen, or to make a qualitative assessment of a sample or specimen. A sample can be a fluid sample, such as a liquid sample. Examples of fluid samples that may be assayed include bodily fluids including but not limited to blood, serum, plasma, saliva, urine, ocular fluid, semen, and spinal fluid; water samples, such as samples of water from oceans, seas, lakes, rivers, and the like, or samples from home, municipal, or industrial water sources, runoff water or sewage samples; and food samples, such as milk or wine. Viscous liquid, semi-solid, or solid specimens may be used to create liquid solutions, eluates, suspensions, or extracts that can be samples. For example, throat or genital swabs may be suspended in a liquid solution to make a sample. Samples can include a combination of liquids, solids, gasses, or any combination thereof, as, for example a suspension of cells in a buffer or solution. Samples can comprise biological materials, such as cells, microbes, organelles, and biochemical complexes. Liquid samples can be made from solid, semisolid or highly viscous materials, such as soils, fecal matter, tissues, organs, biological fluids or other samples that are not fluid in nature. For example, these solid or semi-solid samples can be mixed with an appropriate solution, such as a buffer, such as a diluent or extraction buffer. The sample can be macerated, frozen and thawed, or otherwise extracted to form a fluid sample. Residual particulates can be removed or reduced using conventional methods, such as filtration or centrifugation.

Analytes that can be detected using the devices and methods of the invention can include any molecule of interest. In some embodiments, the analyte is a molecule that can be suspended or dissolved in a liquid. These include molecules such as nucleic acids, amino acids, lipids, saccharides, hormones, proteins, drugs, drugs of abuse, biological warfare agents, toxins, vitamins, steroids, pesticides, industrial chemicals, analogs, derivatives, and metabolites thereof.

In some embodiments, the analyte can be a drug of abuse. The term "drug of abuse" (DOA) refers to a drug that is taken for non-medicinal reasons (which can be for mind-altering effects). The abuse of such drugs can lead to physical and mental damage and (with some substances) dependence, addiction and/or death. Examples of DOAs include but are not limited to cocaine; amphetamines (e.g., black beauties, white bennies, dextroamphetamines, dexies, beans); methamphetamines (crank, meth, crystal, speed); barbiturates (Valium®, Roche Pharmaceuticals, Nutley, N.J.); sedatives (i.e. sleep-aids); lysergic acid diethylamide (LSD); depressants (downers, goofballs, barbs, blue devils, yellow jackets, ludes); tricyclic antidepressants (TCA, e.g., imipramine, amitriptyline and doxepin); phencyclidine (PCP); tetrahydrocannabinol (THC, pot, dope, hash, weed, etc.); and opiates (e.g., morphine, opium, codeine, heroin, oxycodone). Legal drugs that are taken for medical reasons, but for which overdose can easily occur may also be tested for using these strips, for example, tricyclic antidepressants (imipramine and the like) and over the counter products containing acetaminophen.

"Upstream" and "downstream" refer to the liquid flows along the direction of the division. Upstream is located in the upper reaches of the liquid flow on the direction and downstream is located in the lower reaches of the liquid under the direction of flow. Upstream and downstream are a relative concept referring to the liquid from the upper reaches of the position to the lower reaches of the Flow downstream.

I. Devices

The devices described herein can be used for the detection of analytes in samples. In particular, the devices of the invention can be used to determine the presence, absence, or concentration of the analytes using both competitive and non-competitive lateral flow assays. The samples and the analytes to be detected can be any sample or analyte described herein. In some embodiments of the invention, the sample can be saliva and the analyte can be a drug of abuse.

A variety of assays can be used to detect the presence, absence, or concentration of an analyte in a sample. For example, analytes can be detected using labeled binding moieties, chemicals that react with the analyte, light that interacts with the analyte, electrochemical detection, or any combination thereof. In particular, non-competitive assays can utilize binding moieties that immobilize the analyte, which then allow for the analyte to be detected using additional detectable binding moieties to the analyte. Alternatively, competitive assays can utilize analyte mimics that compete with the analyte for binding to immobilized binding moieties that exhibit specific binding to both the analyte and the analyte mimic. Detection of the analyte can be either by labeling of the analyte mimic or the use of detectable binding moieties that bind only to the analyte or the analyte mimic.

Typically, in noncompetitive formats, a signal is produced if the sample contains the analyte, and no signal is produced if the analyte is not present. In competitive formats, a signal can be produced if no analyte is present and no signal if analyte is present.

A. Second Reagent Zone

A second reagent zone can be used in the devices of the invention to mix the sample with reagents, buffers, or other materials. The second reagent zone can be formed of a bibulous material, a non-bibulous material, or any combination thereof. In some embodiments of the invention, the second reagent zone is an adsorbent pad, a piece of filter paper, a membrane, a piece of plastic, or any combination thereof. For example, an adsorbent pad can be fixed to a piece of plastic to form a second reagent zone. The reagent, buffers, or other materials can be dried on the second reagent zone such that the reagents, buffers, or other materials are resuspended or mobilized into solution when the sample is applied to the second reagent zone. The second reagent zone may or may not be directly integrated with a test strip that indicates the presence, absence, or concentration of the analyte. In preferred embodiments, use of a pipette or other transfer devices requiring user intervention are not required to transfer the sample mixed with reagents, buffers, or other materials from the second reagent zone to the test strip for analysis.

The second reagent zone can contain antibodies, antigens, binding moieties, members of binding pairs, buffers, proteins, salts, energy sources, and/or labels. In some embodiments of the invention, a binding moiety in the second reagent zone can be an analyte-binding moiety that binds to the analyte of interest. The binding moiety may or may not be conjugated to a detectable label or a member of a binding pair. An example of a member of a binding pair includes one of streptavidin/biotin, avidin/biotin, or other binding pairs known to those skilled in the art. The binding between the binding pairs can have a dissociation constant less than about 10, 1, 0.1, 0.01, 0.001, 0.0001, 0.00001 micromolar. In some embodiments of the invention, the analyte is an antibody. The binding moiety can be an antigen that binds to the analyte.

In some embodiments of the invention, the second reagent zone can contain lysis buffers, DNAses, proteases, lipases, desiccants, or other reagents that can prepare a sample for analysis. For example, the second reagent zone can contain a protease that can reduce the viscosity of a saliva sample.

As described herein, the second reagent zone can be integrated with a test strip for analysis of the sample in a variety of manners. For example, (a) a second reagent zone can be located on a test strip of the invention that provides a signal indicating the presence, absence or concentration of an analyte, (b) the second reagent zone can be housed within a device that comprises a test strip that is separate from the second reagent zone, or (c) the second reagent zone can be separate from a device that houses the test strip.

The test strip can be integrated with the second reagent zone in a test device. The test device can be configured such that flow of the sample, along with reagents, buffers, or other materials resuspended from the second reagent zone flow to the test strip after a sufficient period of time. The sufficient period of time can allow for sufficient formation of complexes, the sufficient completion of reactions, or sufficient progress toward an equilibrium state. For example, greater than 50, 60, 70, 80, 90, 95, 99, 99.5, 99.9% of total possible complexes or reactions may formed or occur prior to movement of the sample from the second reagent zone to the test strip. In other embodiments of the invention, the sample is in contact with the second reagent zone for greater than about 0.2, 0.5, 0.7, 1, 2, 3, 4, 5, 6, 7, 8, 9, 10, 12, 15, 20, 25, 30, 40, 50, or more minutes prior to contacting the test strip. In other embodiments of the invention, the sample is in contact with the second reagent zone for greater than about 1 to about 30 minutes prior to contacting the test strip. The transfer of sample from the second reagent zone to the test strip can be automated, such that the sample is transferred after about 1, 2, 3, 4, 5, 10, 15, 20, 25, or 30 minutes. The automated step can eliminate the need for intervention by an operator. The step can be automated by a timer or other mechanism that transfers the sample to the test strip after a sufficient period of time. In some embodiments of the invention, the sufficient period of time is indicated by a detectable change in the sample. For example, a color may be generated or another detectable signal can be generated.

The test device can be configured to have a first position that prohibits fluid communication between the second reagent zone and the test strip and a second position that allows fluid communication between the second reagent zone and the test strip.

In other embodiments of the invention, movement of the test device from a first position to a second position transfers the mixture, formed between the sample and the reagents, buffers, or other materials of the second reagent zone, to the test strip. In some embodiments, the second reagent zone may not be in fluid communication with the test strip in the first position as well as the second position. Movement from a first position to a second position can transfer solution between the second reagent zone and the test strip without the second reagent zone and the test strip being in direct fluid communication.

An example of a second reagent zone integrated with a test strip is shown in FIG. 2. As illustrated in FIG. 2, the test device 20 can include a second reagent zone having a second reagent pad 201 that is in fluidic communication with and separated from a lateral flow test element 101 with a sample receiving pad 111, label pad 121, test strip 133 and an absorbent pad 141. These pads can be arranged in this order along the test strip in the direction of liquid sample flow. A test result zone 132 and a result control zone 33 can be located on the test strip 131.

In another embodiment, as illustrated in FIG. 3, the test device includes a second reagent zone and a test element with a sample receiving zone 11, label zone 12 and a test result zone 13. An analyte-binding moiety (Y1) conjugated with a first member (M1) of a binding pair (M1/M2) that is not related to the analyte is moveably dried on the second reagent zone. An analyte-binding moiety can be a molecule that binds to an analyte. The analyte can be the analyte to be detected in the sample. The test element includes a sample receiving zone 11 downstream of the second reagent zone; a label zone 12 with a detectable label (L) conjugated to a second member (M2) of the binding pair; a test result zone 13 where a second analyte-binding moiety (Y2) is immobilized thereon; and wherein the first binding moiety and the second binding moiety can specifically bind the analyte in the liquid sample, as illustrated in FIG. 3A. Y1 and Y2 can both bind to the analyte. When a liquid sample is applied to the second reagent zone of the test device, if the analyte (A) is present in the liquid sample, the analyte (A) can first be bound by the first binding moiety to form a first complex (A:Y1-M1) that can be moved by the liquid sample from the sample receiving zone to the label zone where a second complex will be formed (A:Y1-M1:M2-L) that will also be moved to the test result zone where the second complex will be captured by the immobilized second analyte-binding moiety (Y2) and a positive result can be detected on the test result zone, as illustrated in FIG. 3B, by formation of a detectable complex.

In another embodiment, as illustrated in FIG. 4, the test device includes a second reagent zone and a test element with a sample receiving zone 11, label zone 12 and a test result zone 13. A first binding moiety, which can be an analyte-binding moiety, (Y1) conjugated with a first member (M1) of a binding pair (M1/M2) that is not related to the analyte is moveably dried on the second reagent zone. The test element includes a sample receiving zone 11, at downstream of the second reagent zone; a label zone 12 with a detectable label (L) conjugated to a second binding moiety (Y2); a test result zone 13 where a second member (M2) is immobilized thereon; and wherein the first binding moiety and the second binding moiety can specifically bind the analyte in the liquid sample, as illustrated in FIG. 4A. Y1 and Y2 can both bind to the analyte. When a liquid sample is applied to the second reagent zone of the test device, if the analyte (A) is present in the liquid sample, the analyte (A) will first be bound by the first binding moiety to form a first complex (A:Y1-M1) that will be moved by the liquid sample from the sample receiving zone to the label zone where a second complex will be formed (L-Y2:A:Y1-M1) that will also be moved to the test result zone where the second complex can be captured by the immobilized second member (M2) and a positive result can be detected on the test result zone, as illustrated in FIG. 4B, by forming a detectable complex.

In another embodiment, illustrated in FIG. 5, a test device includes a second reagent zone with an analyte-binding moiety (Y1) conjugated with a first member (M1) of a binding pair that are not related to the analyte in the liquid sample. The second reagent zone can be in fluidic communication with a test element that has a sample receiving zone 11, a label zone 12 with a detectable label (L) conjugated to an analyte mimic (A*), and a test result zone 13 where a second member (M2) is immobilized thereon. The analyte mimic can compete with the analyte for binding to the analyte-binding moiety. All these zones may have this order of arrangement in the direction of the liquid flow, as illustrated in FIG. 5A. The amounts of the first molecule conjugated with the first member and the label conjugated with the analyte mimic can be adjusted. The adjustment can be based on a predetermined concentration (C) such that, e.g., in a drug abuse assay, when the concentration of an analyte is lower than a predetermined concentration (C), the test result zone with a detectable label indicates a negative result (indicated by either presence or absence of a detectable label depending on the assay, e.g., if the assay utilizes competitive binding or not). When the concentration of an analyte is higher than a predetermined concentration (C), the test result zone without a detectable label indicates a positive result (indicated by either presence or absence of a detectable label depending on the assay, e.g., if the assay utilizes competitive binding or not).

When a liquid sample is applied to the second reagent zone, if the concentration of analyte (A) is higher than the pre-determined concentration (C), most of the analyte-binding moiety (Y1) conjugated with the first member (M1) will bind to the analyte (A) to form a complex (A:Y1-M1). The complex with the remaining amount of the analyte (A) in the liquid sample, if any, will be moved with the liquid sample from the sample receiving zone to the label zone in which the label and the analyte mimic will competitively bind the first complex. Since most of the conjugate (Y1-M1) may be bound by the analyte, the label and the analyte mimic may not easily bind to the conjugate. When the liquid sample with the complex reaches the test result zone where the complex will be captured by the immobilized second member (M2), a positive result will be detected via detecting the presence or absence of the label at the test result zone.

In contrast, if the concentration of the analyte is lower than the pre-determined concentration (C), a part of the analyte-binding moiety (Y1) conjugated with the first member (M1) will bind to the analyte A to form a complex (A:Y1-M1), and the remaining unbound first binding moiety (Y1) conjugated with the first member (M1) will flow with the complex to reach the label zone downstream of the second zone. At the label zone, the rest of the conjugate (Y1-M1) will be bound by the analyte mimic that is conjugated with a detectable label to form a second complex (L-A*:Y1-M1). Both of the complexes will be moved to the test result zone where the immobilized member (M2) will capture the first member (M1) of the complex with a label, forming a detectable complex, and the complex without any label. A negative result is determined by detecting the presence or absence of label on the test result, as illustrated in FIG. 5B.

In some embodiments of the invention, the separate second reagent zone is located within a test tube or sample cup. The sample, mixed with reagents, buffers, or other materials in the second reagent zone can then be transferred or moved, e.g., by a pipette or other transfer device, to a test strip for analysis.

In other embodiments, the second reagent zone may not be in the same device with the test element, and can be in another collection well that is separate from the casing. As disclosed in this present invention, the strip 2011 contains Y1 and M1, and the test element contains M2. For example, the second reagent zone 201 can be located in a test tube that is used to receive a liquid sample. After the reagents on the second reagent zone 201 react with the sample, the mixture can be added onto the test element for conducting the assay. Sample collection devices are disclosed in the U.S. Pat. Nos. 6,780, 160, 7,048,693, 5,234,001, 5,830,154, 5,786,427, 5,573,099, and US Patent Publication No. US 2001/0008614, and PCT Publication No. WO2005008216, all of which are incorporated herein by reference.

B. Test elements

The test element can be lateral flow test strips, which are widely available for testing a broad range of analytes. However, any suitable test element can be used in the present invention.

Figure 1C:
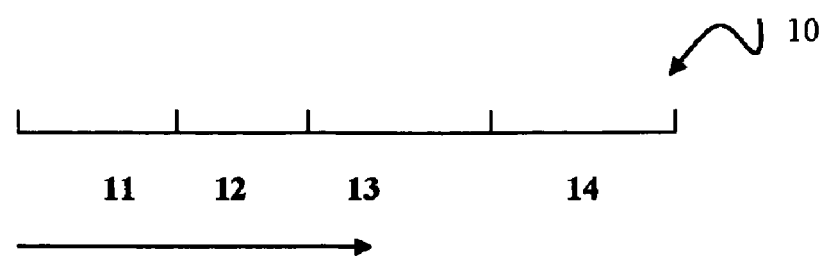
FIG. 1C is a perspective view of a lateral flow device showing a sample receiving zone 11, label zone 12, test result zone 13 and an absorbent zone 14 that are arranged in the direction of the liquid flow.

A variety of test elements can be incorporated into the present invention. One type of test element is a test strip. Test strips are available in a variety of formats, such as immunoassay or chemical test format. The tests strips can be for detecting analytes of interest in a sample, such as a drug of abuse or a metabolite suggestive of health status. Test strips can also be configured for either noncompetitive or competitive assay format. In some formats, as illustrated in FIG. 1C, the test strips have a bibulous material having a first reagent zone that is upstream of a test result zone 13, which has an analyte-binding moiety. In a preferred embodiment, an absorbent zone 14 is downstream of the test result zone 13. All these zones are arranged in the direction of liquid flow. Certain amount of reagent for conducting the assay is treated on the sample receiving zone, such as a buffer solution to pre-treat the liquid sample. The label zone may have any detectable label, such as gold particles, latex particles or water-soluble dye, which can be conjugated to an analyte-binding moiety. The first reagent zone has a sample application zone 11, a label zone 12, and a test result zone. The sample is applied to the sample application zone and flows into the reagent zone by capillary action. In the reagent zone, the sample dissolves and mixes with reagents necessary for detection of the analyte (if present). The sample, now carrying the reagents, continues to flow to the test result zone. Additional reagents are immobilized in the test result zone, such as an analyte-binding moiety for the analyte. These reagents react with and bind to the analyte (if present) or one of the first reagents from the reagent zone. Labels for providing the detectable signal can be present in the reagent zone, or in a separate label zone.

The zones can be arranged as follows: sample application zone, one or more reagent zones, one or more test result zones, one or more test result control zones, one or more adulteration zones, and one or more fluid absorbing zone. In some embodiments, the test results determination zone includes a control zone. All of these zones, or combinations thereof, can be provided in a single strip of a single material. Alternatively, the zones are made of different materials and are linked together in fluid communication. For example, the different zones can be in direct or indirect fluid communication. In this instance, the different zones can be joined end-to-end to be in fluid communication, overlapped to be in fluid communication, or be communicated by another member, such as a joining material, which is preferably bibulous such as filter paper, fiberglass or nitrocellulose. In using a joining material, a joining material may communicate fluid from end-to-end joined zones or materials including such zones, end-to-end joined zones or materials including such zones that are not in fluid communication, or joined zones or materials that include such zones that are overlapped (such as but not limited to from top to bottom) but not in fluid communication.

When the test element is a test strip, it may be made of bibulous or non-bibulous material. A test strip can include more than one material, which are then in fluid communication. One material of a test strip may be overlaid on another material of the test strip, such as for example, filter paper overlaid on nitrocellulose. Alternatively or in addition, a test strip may include a region comprising one or more materials followed by a region comprising one or more different materials. In this case, the regions are in fluid communication and may or may not partially overlap one another. The material or materials of the test strip can be bound to a support or solid surface such as a supporting sheet of plastic, to increase its handling strength.

Alternatively, the test strip can be a device that utilizes capillary action to drive the movement of fluid from the first reagent zone to the test result zone. For example, two surfaces of non-bibulous materials can be placed in close proximity such that a capillarity can be formed between the two surfaces.

The test strip can have a sample application zone. The sample application zone can absorb the sample that may be mixed with reagents from the second reagent zone. In some embodiments of the invention, the sample application zone can absorb the entire sample applied to the second reagent zone. In other embodiments of the invention, the sample application zone can absorb a fixed volume of sample. Alternatively, only a fixed volume is delivered from the second reagent zone to the test strip by the devices of the invention. For example, movement of the test device from a first position where the second reagent zone is not in fluid communication with the test strip to a second position where the second reagent zone is in fluid communication with the test strip transfers a fixed volume of sample to the sample application zone.

The first reagent zone can have a label zone containing a label thereon. The label can be a detectable label, such as an optically detectable label, an electrically detectable label, a label that generates a detectable label through a chemical reaction, label that is a signal producing system, or any other type of label known to one skilled in the art. For example, a label can be a gold particle, a colored dye, or an enzyme that generates a detectable label.

In embodiments where the analyte is detected by a signal producing system, such as by one or more enzymes that specifically react with the analyte, one or more components of the signal producing system can be bound to the test result zone of the test strip material in the same manner as specific binding members are bound to the test strip material, as described herein. Alternatively or in addition, components of the signal producing system, such as labeled reagents, that are included in the sample application zone, the reagent zone, or the test result zone of the test strip, or that are included throughout the test strip, may be impregnated into one or more materials of the test strip. This can be achieved either by surface application of solutions of such components or by immersion of the one or more test strip materials into solutions of such components. Following one or more applications or one or more immersions, the test strip material is dried. Alternatively or in addition, components of the signal producing system that are included in the sample application zone, the reagent zone, or the test result zone of the test strip, or that are included throughout the test strip, may be applied to the surface of one or more test strip materials of the test strip as was described for labeled reagents.

The label can be conjugated to an analyte mimic, an analyte-binding moiety, or a member of a binding pair. The analyte-binding moiety can be distinct from the analyte-binding moiety of the second reagent zone, however both analyte binding moieties may both bind to the analyte.

An analyte mimic A* may be an analyte analogue that is capable of forming a complex with an antibody. The antibody may also form a complex with the analyte. In some embodiments, the analyte mimic and the analyte can compete for binding to the antibody. In other embodiments of the invention, the analyte and analyte mimic exhibit competitive binding to the antibody. The analyte and the analyte mimic may exhibit similar binding affinities to the antibody, or the binding affinities can be different. The binding affinity between the antibody and the analyte mimic can be stronger or weaker than the binding affinity between the antibody and the analyte. The binding affinity between the antibody and the analyte mimic can be higher or lower than the binding affinity between the antibody and the analyte. The binding affinities can be selected to adjust a detection threshold using methods known to one skilled in the art. For example, binding molecules, such as binding moieties or members of binding pairs, can be mutated by random or non-random techniques.

The analyte mimic may be a fragment of an analyte, the fragment retaining an epitope of the analyte. The label can be linked with a linker that links the label and the analyte mimic. Typically, a linker has a binding site that is not present on the analyte, analyte mimic (A*) or label (L). For example, the binding site may be an epitope capable of being recognized by an antibody that does not recognize either the analyte, analyte mimic or the label. In some embodiments, the linker is capable of being recognized by antibodies that also do not recognize the binding sites of other linkers that may be present. Examples of such linkers include but are not limited to bovine serum albumin (BSA), keyhole limpet hemocyanin-inconjugate (KLH), and bovine benzoylecgonine (BBG), bovine thyroglobulin (BTG), hen egg-white lysozyme (HEL), ovalbumin (OVA), sperm whale myoglobin (SWM), tetanus toxoid (TT), methylated bovine serum albumin (mBSA), Rabbit Serum Albumin (RSA).

The test strip can comprise a test result zone. The test result zone can have one or more test lines and one or more control lines. The test line can be used to determine the presence, absence, or concentration of the analyte in the sample. The control line can be used to determine whether the result in the test line can be used. In some embodiments of the invention, the control lines can comprise a positive control line and a negative control line. Reagents that can bind to the control line can be disposed in the second reagent zone or the first reagent zone in a dry state. In some embodiments of the invention, the absence of a line in the control line can indicate a faulty assay.

The test line can bind to a complex formed in solution, such that the complex becomes immobilized. The complex can comprise a label that is detectable. The complex can include the analyte and a detectable label. In other embodiments, the complex can include the analyte mimic and a detectable label. The label can be any label described herein. When the complex includes a member of a binding pair, the test line can comprise the other member of the binding pair. Alternatively, the test line can have an analyte binding moiety that can bind to the complex.

C. Housing

The second reagent zone and the test strip can be positioned within a housing. The housing can provide support to the test strip and the second reagent zone. Additionally, the housing can interface with a sample collector such that sample can be transferred from the sample collector to the second reagent zone. The housing can control fluid communication or the transfer of fluids between the second reagent zone and the test strip.

The housing can have a sample extraction plate that allows for sample to be removed from a sample collector. In some embodiments, the sample collector comprises an adsorbent material that can release its contents, e.g., a saliva sample, when compressed. The sample extraction plate can provide a stable or rigid structure to compress the sample collector against.

The housing can also have a confirmation well. The confirmation well can store sample before or after mixture with the reagents from the second reagent zone. In some embodiments, the confirmation well can be sealed after the sample is added to the confirmation well. Sample can be recovered from the confirmation well for later analysis.

In some embodiments of the invention, the test device can have a valve that controls flow between the second reagent zone and the test strip. Alternatively, fluid can be transferred between the second reagent zone and the test strip by a device that collects a portion of the sample in contact with the second reagent zone and moves to be in fluid communication with the test strip.

The housing that contains the test strip can have a viewing window to observe the results of the assay. The test strip can be aligned within the housing such that test lines and/or control lines on the test strip are positioned beneath the viewing window. The viewing window can have an optically transparent material or the viewing window can be a cut out in the test device housing.

Figure 6:
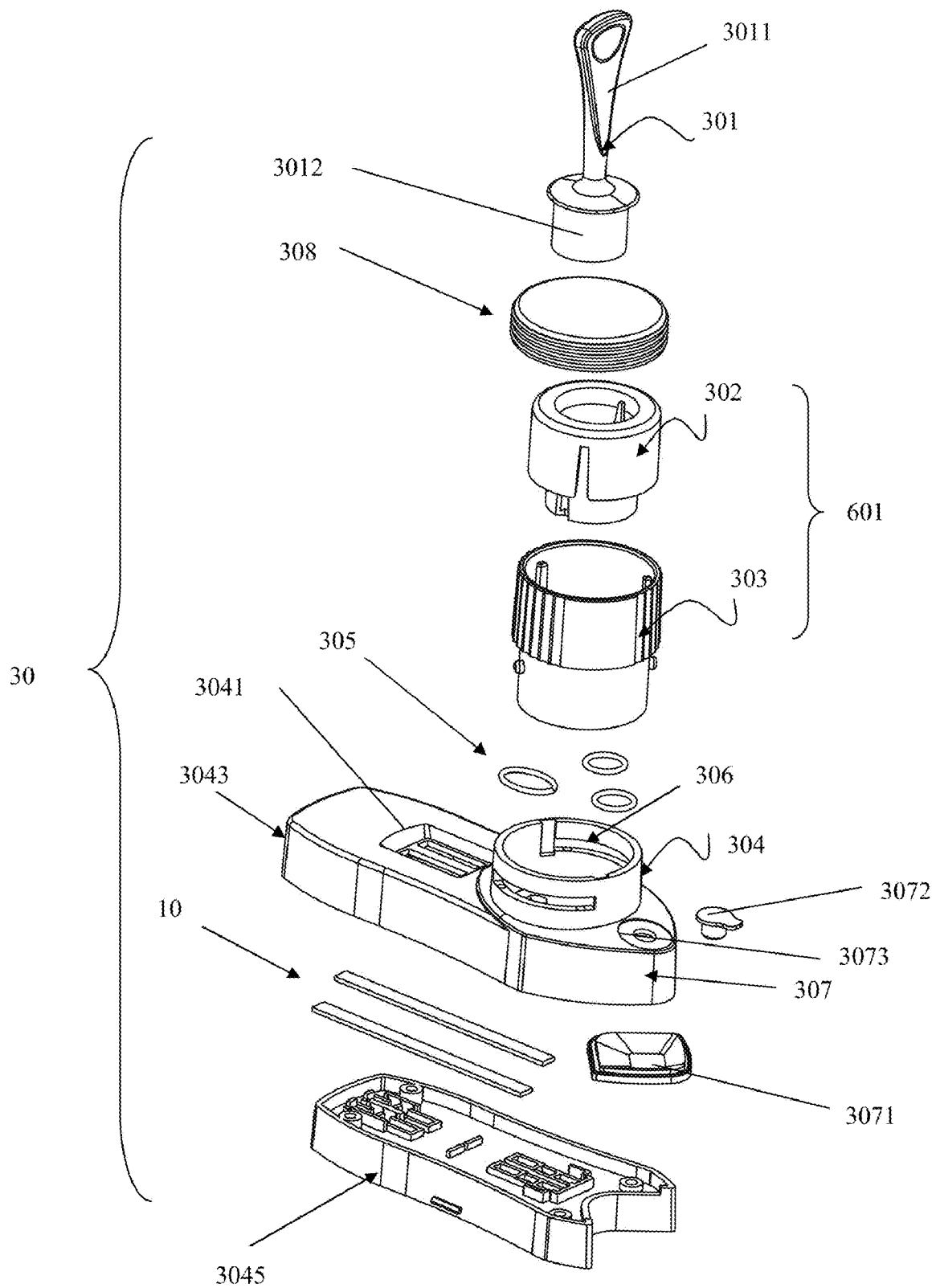
FIG. 6 is a perspective view of a test device with a sample collection well 302 that is connected to a casing with a test element 10 therein, wherein a second reagent zone is configured to be within the sample collection well 601.
Figure 7:
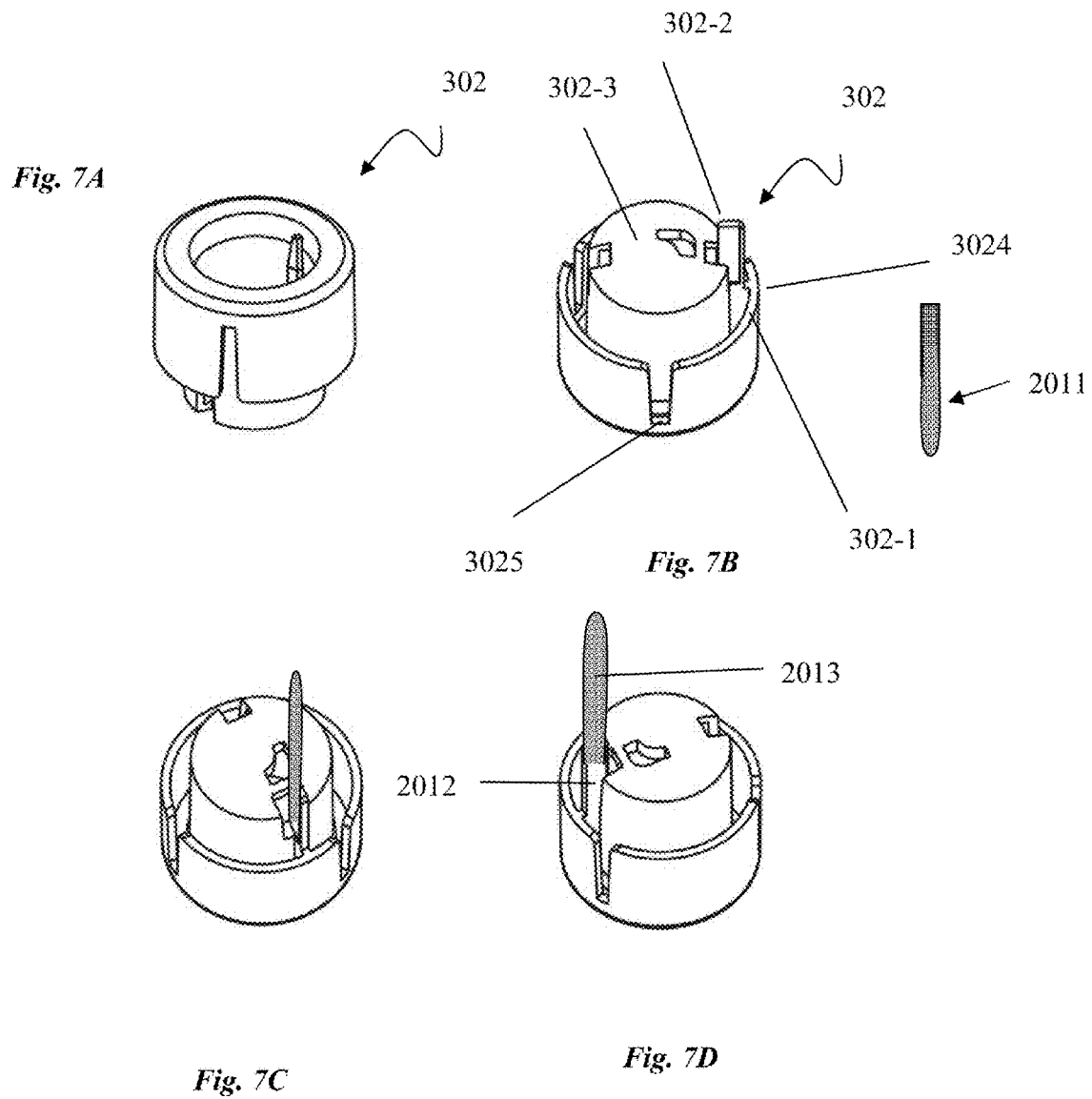
FIG. 7A is a perspective view of the test device comprising a sample receiving well 302 with a second reagent zone on the porous member 2011.
FIG. 7B is a perspective view of an unassembled sample receiving well and a porous member 2011.
FIG. 7C is a perspective view of the sample receiving well that is attached to the porous member 2011 at a piece 3024.
FIG. 7D is a perspective view of the sample receiving well that is attached to the porous member 2011 at a piece 3024.
Figure 8:
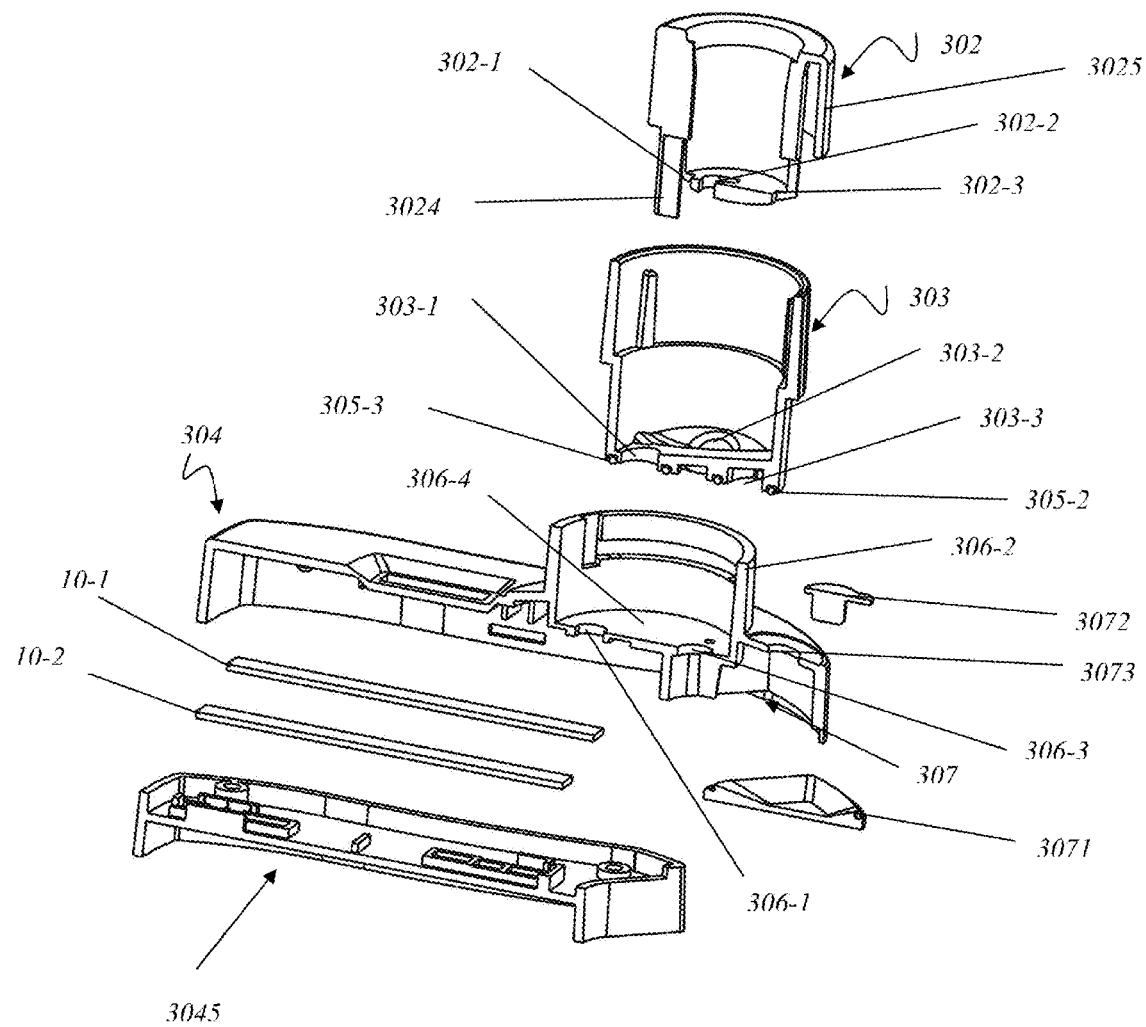
FIG. 8 is a section view of the test device.

FIGS. 6, 7 and 8 show a housing with a casing 304 and a sample collection well 601. The test element 10 inside the casing 304 and the second reagent region 201 located in the sample collection well 601 are in fluid communication, meaning that the fluid from the sample collection well 601 can flow to the test element 10. This kind of fluid communication can be due to gravity or a fluid conducting structure between the sample collection well 601 and the test element 10 configured to make the liquid flow from the sample collection well to the test element. With reference to FIG. 8 in detail, the casing 304 has a result reading window 3041 which is opposite to the test result zone of test element 10 and a sample port 306, which comprises two sample leading ports 306-1 and 306-3. When the sample fluid is flowing from the sample leading port 306-1 and reaches the sample receiving zone of the test element 10, the analysis test can be finished.

In certain embodiments, the sample collection well 601 can include a first collection chamber 302 and a second collection chamber 303. The first collection chamber is composed of two opening ends: one opening end is for receiving a liquid sample or a sample, and another opening end has fluid passage holes 302-1, 302-1 or 302-3 as illustrated in FIG. 7A-7D. A vertical piece or erect balk 3024 can be located opposite to one of the fluid passage holes, such as 302-1. One end of the erect balk 3024 can be fixed on the outer wall of the first collection chamber 302; the opposite end of the balk can be extended through one of the fluid passage holes, such as 302-1. The second reagent region 201 comprises a porous strip 2011 with two ends 2013 and 2012. The strip can be fixed or contacted onto the surface of the balk as to make the end of the strip extend to the bottom of the second collection chamber 303 through the hole 302-1. Another side of the strip 2011 called the test portion 2013 can be extended through the fluid passing passage 320-1 and reach to the bottom of the second sample collection chamber 303. The strip 2011 with special substance like protein treatment can be made of bibulous material, such as fiberglass, filter paper or cellulose fiber and so on. With the reference of FIG. 9, the second reagent region 201 may exist in other formats in the sample collection well 601. For example, the strip 2011 can be directly placed on the bottom of the second sample collection chamber 302. In some other embodiments, the strip 2011 can be deposited on an isolated position formed by the first collection chamber 302 and the second collection chamber 303. The main purpose for this arrangement of the second reagent zone is so that it can be in fluid communication with the liquid sample in the collection well 601. The strip 2011 can be designed such that it is either fully or partially in contact with the liquid sample. In addition, the method of placing material on the second reagent region can be varied, e.g., the second reagent region can be directly treated, sprayed or dabbed. In these above embodiments, a molecule or binding moiety having specific binding to an analyte is moveably dried on the second reagent zone, similar to the porous strip 2011. The binding moiety can be conjugated with a first member of (M1) a binding pair (M1/M2) that is not related to the analyte. Additionally, the second reagent zone can further comprise other reagents or buffers for conducting the assay.

Figure 9:
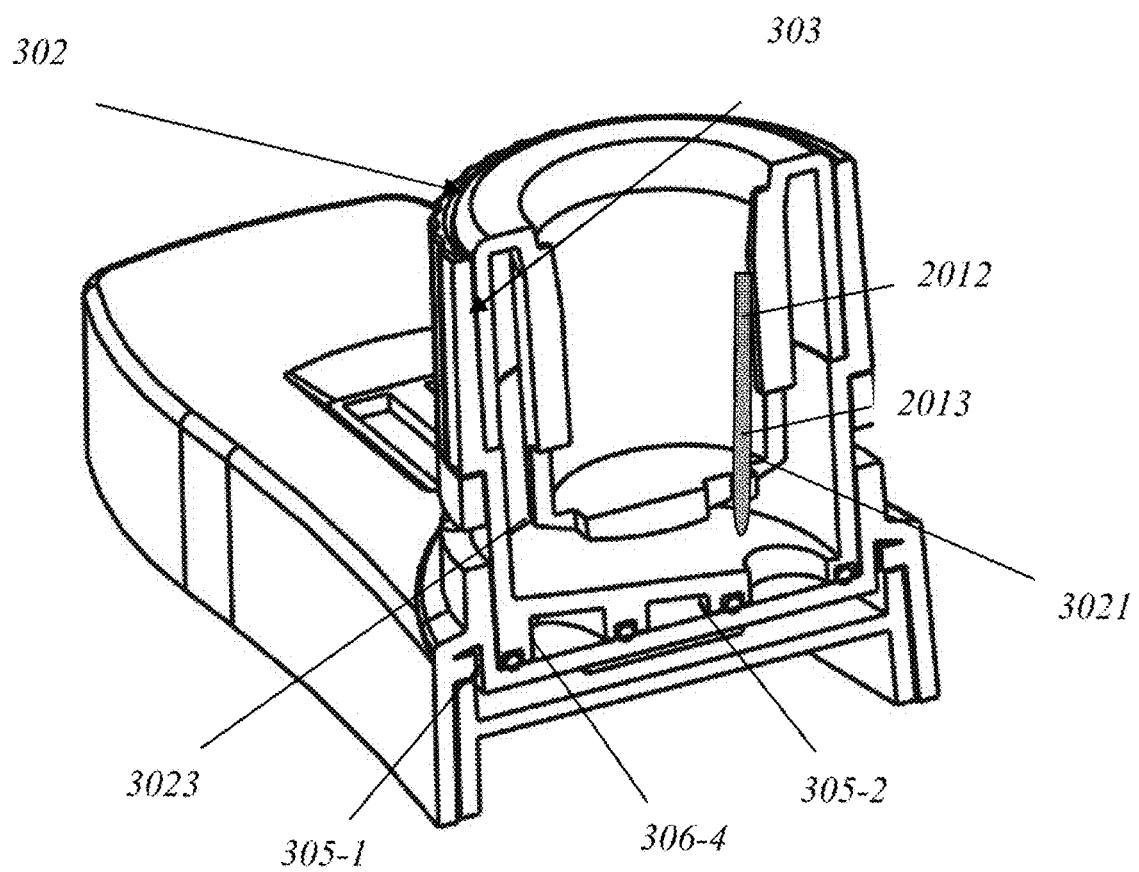
FIG. 9 is a section view of the test device before applying a liquid sample to the sample receiving well.
Figure 10:
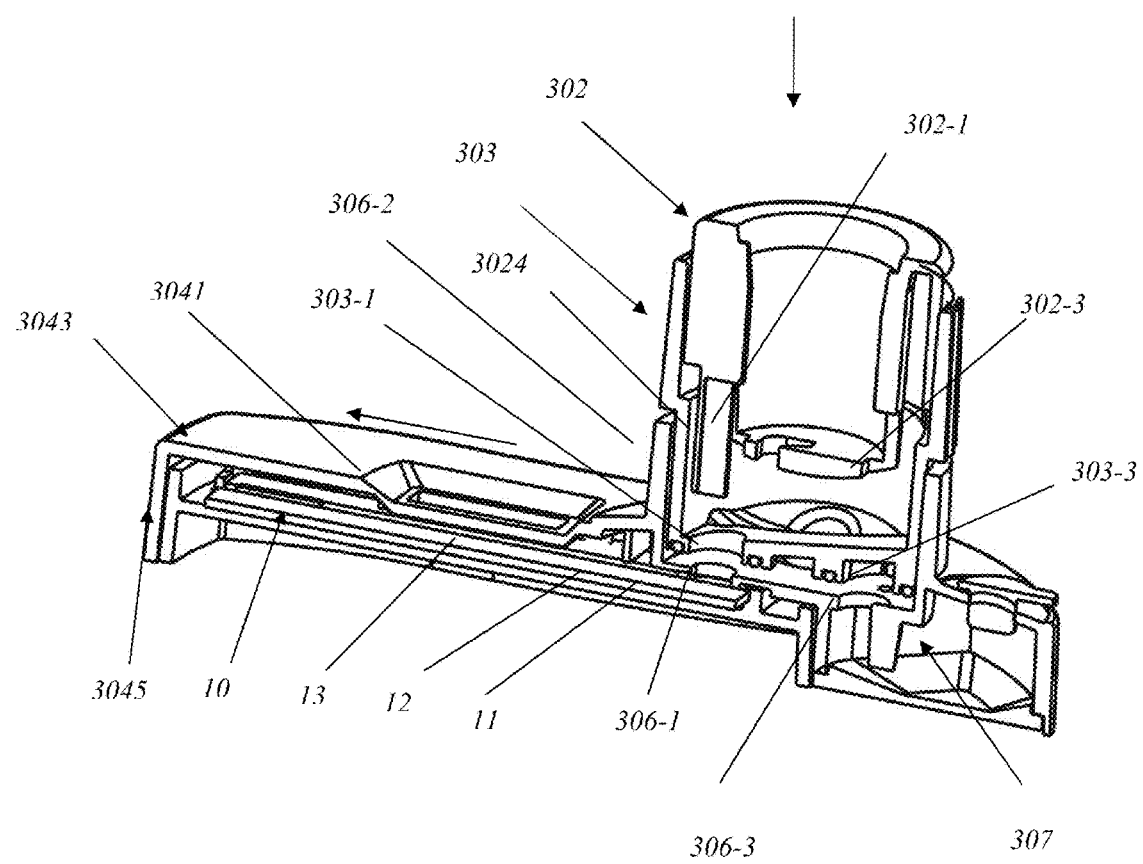
FIG. 10 is a section view of the test device after applying a liquid sample to the sample receiving well.

With the reference to FIGS. 8, 9 and 10, the sample collection well 601 is connected with the reservoir 304 and come whole by a block ring 306-2 of the sample leading port 306. The second collection chamber 303 provides many liquid passage holes 303-1, 303-2 and 303-3, which are fixed with sealing rings 305-1, 305-2 and 305-3 at one end. In detail, the sample collection well 601 is situated in the sample leading port 306 on the top portion 3043 of the casing. The sample port 306 is integral to the top portion 3043 of the casing and has a guide slot cut therein parallel to the upper rim of the sample port 306. The second collection chamber 303 has a one guide pin extending from its exterior surface through the guide slot of the reservoir 304. Two or more guide slots and guide pins can be located on the reservoir 304 and the second collection chamber 303. The second collection chamber 303 and sample port 306 are adapted so that the second chamber can be rotated in the sample port 306. A test device with a collection well can be found in other published applications, such as published application No. 2005/0180882A1.

This invention provides an example of drug abuse testing in a saliva sample. With the reference to FIG. 9, this figure shows the phase of sample collecting before assaying. The first collection chamber 302 is located in the second collection chamber 303. The liquid passage holes 303-1, 303-2 and 303-3 of the second collection chamber 303 are sealed with against bottom plate 306-4 of the sample leading region 306, instead being in fluidic communication with the sample leading ports 306-1, 306-3 of the sample leading region 306. Enhancing the sealing capability between the said two parts, other sealing rings 305-1, 305-2 and 305-3 can be fixed on a corresponding position of the passages for fluidic communication.

II. Methods

The methods of the invention can be used to determine the presence, absence, or concentration of an analyte in a sample. Samples can be collected from a test subject, such as a human or an animal, and then analyzed using the methods described herein. Samples can be incubated with a first set of reagents to form a mixture, and the mixture can then be applied to a test strip for analysis. The test strip can have an area with a second set of reagents and an analysis zone. The samples can be transferred to the test strip after a certain period of time. In other embodiments of the invention, the sample is transferred to the test strip after the sample has had sufficient time to interact with the first set of reagents, such that complexes can be formed, reactions can be completed, or equilibrium is achieved. In some embodiments of the invention, the sample is transferred with minimal chance for an operator to introduce additional error into the assay. For example, the operator can allow for fluid communication between the second reagent zone and the test strip or transfer sample from the second reagent zone to the test strip by rotating a piece of the test device from a first position to a second position, pushing a button, or moving a switch from a first position to a second position. Alternatively, the test device can have a timer that automatically transfers the sample from the second reagent zone to the test strip after a period of time. The period of time can be any period of time described herein.

The mixture can be applied to a sample application zone on the test strip, as described herein. The mixture can move from the sample application zone to a first reagent zone that has a second set of reagents. The mixture can bind to reagents or other binding moieties in the first reagent zone to form complexes with detectable labels, described herein. For example, a labeled analyte mimic can compete with an analyte for binding to an analyte-binding moiety.

Once the complex with the detectable label is formed, the complex can move with the mixture to a test results zone. The test results zone can have one or more tests lines and one or more control lines that can be used to determine the presence, absence, or concentration of the analyte in the sample. The results of the assay can be qualitative or quantitative. For example, the presence of a line on a test line can indicate either the presence or absence of the analyte in the sample. Alternatively, the concentration of analyte in the sample can be determined by analyzing the test line. For example, a greater amount of detectable label can be present on the test line when greater amounts of analyte are contained within the sample. The test line can be analyzed visually or spectrophotometrically using methods known to those skilled in the art to quantitatively determine the concentration of the analyte in the sample.

The methods of the invention can provide for increased assay sensitivity and accuracy. The increased sensitivity and accuracy can be a result of allowing the sample to incubate with the reagents in the second reagent zone for a sufficient period of time to react with analytes in the sample. The analytes in the sample can have a concentration of less than about 500, 300, 200, 100, 50, 10, 1, 0.5, 0.1, 0.05, 0.01, 0.005, 0.001, 0.0005, 0.0001 micromolar.

The methods of the invention can allow for the detection threshold to be easily adjusted, above which will indicate a positive assay result or a negative assay result. For example, the amount of any of the binding moieties or binding pairs disposed in any region of the test device can be altered. Additionally, the binding affinities between the binding moieties, analytes, and binding pairs can be selected to adjust detection thresholds.

FIGS. 6-10 show a test device that can be used in the methods of the invention to detect an analyte in a sample. The steps for using a test device for detecting an analyte in a liquid can be as follows: first, place the absorbent member 3012 of the sample collector 301 in the mouth of a test subject to absorb sufficient saliva from the mouth; insert the absorbent member 3012 into the first collection chamber 302 of the sample collection well 601 and compress the absorbent member to extract the sample from the absorbent member into the first chamber 302. The extracted sample can flow into the second collection chamber 303 through the sample passage holes 302-1, 302-2, and 302-3. In the second collection chamber 303, the reagent on the strip 2011 can contact the liquid sample for a period of time. In the cross-sectional view, it can be seen that when the sample collection well 601 is in the first position, the outlets of the first collection chamber 302 and the inlets of the second collection chamber 303 are aligned, forming a passage for fluid communication in the lower chamber of the sample collection well. The strip 2011 can then be in fluid contact and react with the saliva sample. After a suitable reaction time, such as 10 s, 20 s, 30 s, 1 min, 2 min, 3 min, 4 min, 5 min, 6 min, 7 min, 8 min, 9 min, 10 min, 15 min, 20 min, 30 min, 45 min, or 60 min the sample collection well 601 can be rotated to a second position. In this second position, the liquid passing passage 303-1 is in communication with the sample leading port 306-1. Similarly, the liquid passing passage 303-3 is communicating with the sample leading port 306-3. Thus, fluid remaining in the lower chamber of the sample collection well 601 flows into the test compartment and contacts with the test element 10. When the sample fluid comes into contact with the test element 10, the fluid is absorbed by the test element 10 and the test element assay begins. Assay times may vary depending on the sample consistency or viscosity and the test element used.

If the sample contains any drug molecule, a positive result may be determined by a lack of a line in the test result zone of the test element 10. If a drug molecule is not present in the sample, a negative test result can be observed through the window 3041 of the casing 304, which can be uncovered or covered by a transparent material.

This invention illustrates another (and optional) step of using the device, capping the device. The saliva sample may also be directed to flow into a confirmation chamber 307 via the sample leading port 306-3, for further confirmation of the saliva sample tested. Cap 308 can be placed on top of the sample collection well 601. The reservoir may be sealed by the cap. The device may now be shipped to another location for confirmation testing.

For confirmation testing, the orifice seal 3072 can be removed or broken and an aliquot of sample can be removed from the reservoir via the orifice 3073. The confirmation chamber can be formed from a bottom 3071 and sidewalls. The abovementioned saliva testing is an example to illustrate how the present invention can be used. Besides saliva testing, the present invention can also be used in many other applications including but not limited to whole blood testing, urine testing, and fecal testing.

A test device described herein can be used for detecting one or more analytes in a sample. While preferable embodiments of the invention have been shown and described herein, it will be obvious to those skilled in the art that such embodiments are provided by way of example only. The devices and/or methods of the invention can be employed individually or combined with other devices, methods, and/or systems in manners known to those skilled in the arts for detection of one or more analytes in a sample.

EXAMPLES

Example 1

BZO Testing in Saliva Sample

Part One: Test Elements and Device Assembly

With reference to FIGS. 2, 6, and 7, the present invention illustrates the method of assembling the test devices.

NC Membrane

Two lines, a test line and a control line, can be formed on a NC or nitrocellulose membrane so that the membrane can be used as a test pad. The test line is formed by coating the membrane with IgG and streptavidin-IgG solution. The control line is formed by coating the membrane with Goat Anti-Rabbit IgG solution. Both of the fixing treatments are performed by an automatic spray machine. The concentrations of the reagents of both the test line and the control line is 0.3 mg/ml. The buffer is PBS buffer. After coating, the NC membrane is dried in a 37° C. oven.

Conjugate Pad

The conjugate pad can be made of polyester membrane. BZO hapten antigen linked with BSA and gold colloid and Rabbit IgG antibody with gold colloid are placed on the polyester membrane. The optical density (OD) of the reagent solution is 75, 1×PBS with 1% BSA as a diluent. After reagent treatment, the treated polyester membrane is dried in a 37° C. oven.

Sample Receiving Pad

Sample receiving pad can be made of glass fiber. The reagents on the sample receiving pad are: Borax (0.07M/L), Tween20 (1%), Cholic Acid (1%), Tris (0.1M). After reagent treatment, the treated glass fiber is dried in the 37° C. oven.

Test Element Assembly

With reference to FIG. 2, parts of the test element can be assembled as shown. In detail, the sample receiving pad is upstream of the conjugate pad, the conjugate pad is located between the samples receiving pad and the test pad, and the absorption pad is located below the test pad. All the pads are supported by a non-bibulous piece.

The Second Reagent Region

This second reagent region contains a strip 2011, which consists of a non-bibulous affix portion 2012 and a bibulous test portion 2013. The reagents, which are treated on the polyester membrane contain: anti-BZO antibody conjugated with Biotin, 1×PBS and 1% BSA, and the reagents then form a terminal solution with a concentration of 0.15 mg/ml. This piece of polyester membrane is then dried in a 37° C. oven. Finally, the affix portion 2012 is connected together with the test portion 2013.

Device Assembly

With reference to FIGS. 6, 7 and 9, the affixing portion 2012 of the strip 2011 is adhered to the erect balk 3024 of the first sample collection chamber 302. The test portion extends through the liquid hole 302-1 and reaches the bottom of the second sample collection chamber 303. With reference to FIG. 9, the sample collection well 601 is fixed on the block ring 306-2 of the sample leading region 306, which is located on the casing 304. The bottom of the sleeve is located on bottom plate 306-4 of the sample leading region 306. The test element is deposited between the upper portion of the casing 3043 and the lower portion of the casing 3045. The test line of the test element 10 is positioned relative to the result reading window; and the sample receiving region is positioned relative to the sample leading port 306-1. Assembly of the test device may be completed when the upper portion of the casing 3043 and the lower portion of the casing 3035 are attached to each other.

Part Two: Strip and Device Assembly Comparison

In contrast with the above mentioned strip, the conjugate pad of the comparison strip is treated with anti-BZO antibody. The optical density (OD) of the reagent solution is 75, 1×PBS with 1% BSA as the diluent. After treatment with reagent, the conjugate pad of the comparison strip can be dried in a 37° C. oven.

The test membrane is treated with BZO hapten at the concentration of 0.3 mg/ml. The optical density (OD) of the reagent used is 75OD, 1×PBS with 1% BSA as the diluent buffer. After the reagent treatment, the treated polyester membrane can be dried in a 37° C. oven.

The saliva sample is mixed with BZO at a concentration of 5 ng/ml, 7.5 ng/ml (cut-off), 10 ng/ml, 12.5 ng/ml, 15 ng/ml, or 30 ng/ml. All the detection results are read after 10 minutes. The cut-off value determines when a result should be read as positive. For example if the concentration of the analyte is higher than the cut-off concentration, the result should be positive; whereas if the concentration of the analyte is lower than the cut-off concentration, the result should be negative.

Assay Operation for the Test Device

First, all the devices may be positioned as illustrated in FIG. 9. As shown in FIG. 9, the bottom of the second sample collection chamber 303 of the sample collection well 601 is sealed against the bottom plate 306-4.

Second, the sample is added to the sample collector and the sample specimen is allowed to react with the reagent contained in the second reagent zone of the sample collector for one minute.

The sample collection well 601 is rotated and the saliva sample flows from the sample collection well to the sample receiving zone of the test strip and complete the reaction.

The results are recorded after 10 minutes.

The results from using a conventional device are shown in Table 1.

TABLE 1

| BZO Sample | Treatments | | | Result | | | | | | Real result | | | Detection Ratio | | |
|---|---|---|---|---|---|---|---|---|---|---|---|---|---|---|---|
| | | | | Negative | | | Positive | | | | | | | | |
| | Lot #1 | Lot #2 | Lot #3 | Lot #1 | Lot #2 | Lot #3 | Lot #1 | Lot #2 | Lot #3 | Lot #1 | Lot #2 | Lot #3 | Lot #1 | Lot #2 | Lot #3 |
| Negative sample | 10 | 10 | 10 | 10 | 10 | 10 | 0 | 0 | 0 | 10 | 10 | 10 | 100% | 100% | 100% |
| 5 ng/ml | 10 | 10 | 10 | 10 | 10 | 10 | 0 | 0 | 0 | 10 | 10 | 10 | 100% | 100% | 100% |
| 7.5 ng/ml | 10 | 10 | 10 | 10 | 10 | 10 | 0 | 0 | 0 | 10 | 10 | 10 | 100% | 100% | 100% |
| 10 ng/ml (Cut off) | 10 | 10 | 10 | 9 | 10 | 10 | 1 | 0 | 0 | N/A | N/A | N/A | N/A | N/A | N/A |
| 12.5 ng/ml | 10 | 10 | 10 | 9 | 9 | 10 | 1 | 1 | 0 | 1 | 1 | 0 | 10% | 10% | 0 |
| 15 ng/ml | 10 | 10 | 10 | 8 | 9 | 10 | 2 | 1 | 0 | 2 | 1 | 0 | 20% | 10% | 0 |
| 30 ng/ml | 10 | 10 | 10 | 8 | 9 | 9 | 2 | 1 | 1 | 2 | 1 | 1 | 20% | 10% | 10% |

Test results using the devices and methods of the invention are shown in Table 2.

TABLE 2

| BZO sample | Treatments | | | Result | | | | | | Real result | | | Detection Ratio | | |
|---|---|---|---|---|---|---|---|---|---|---|---|---|---|---|---|
| | | | | Negative | | | Positive | | | | | | | | |
| | Lot #1 | Lot #2 | Lot #3 | Lot #1 | Lot #2 | Lot #3 | Lot #1 | Lot #2 | Lot #3 | Lot #1 | Lot #2 | Lot #3 | Lot #1 | Lot #2 | Lot #3 |
| Negative sample | 10 | 10 | 10 | 10 | 10 | 10 | 0 | 0 | 0 | 10 | 10 | 10 | 100% | 100% | 100% |
| 5 ng/ml | 10 | 10 | 10 | 10 | 10 | 10 | 0 | 0 | 0 | 10 | 10 | 10 | 100% | 100% | 100% |
| 7.5 ng/ml | 10 | 10 | 10 | 10 | 10 | 10 | 0 | 0 | 0 | 10 | 10 | 10 | 100% | 100% | 100% |
| 10 ng/ml (Cut off) | 10 | 10 | 10 | 5 | 5 | 6 | 5 | 5 | 4 | N/A | N/A | N/A | N/A | N/A | N/A |
| 12.5 ng/ml | 10 | 10 | 10 | 3 | 3 | 4 | 7 | 7 | 6 | 7 | 7 | 6 | 70% | 70% | 60% |
| 15 ng/ml | 10 | 10 | 10 | 2 | 2 | 2 | 8 | 8 | 8 | 8 | 8 | 8 | 80% | 80% | 80% |
| 30 ng/ml | 10 | 10 | 10 | 0 | 1 | 0 | 10 | 9 | 10 | 10 | 9 | 10 | 100% | 90% | 100% |

RESULTS AND DISCUSSION

In some aspects, the present invention provides a device and a method for detecting a low concentration of analyte in a sample fluid with high sensitivity and high accuracy. The device and methods of the present invention retain the specificity for detecting an analyte in a sample fluid. To compare, for example, when the BZO concentration is as low as about 12.5 ng/ml, the known detection methods generally lead to 28 negative and only 2 positive results. The detection ratio is about 10%. However, the methods and devices disclosed in the present invention may give 20 positive results and 10 negative results. The detection ratio of the present invention is about 60%-70%. In another example, when the BZO concentrations are 12.5 and 15 ng/mL, the detection ratio of the known existing device is about 10%-20%. However, the detection ratio of the device of the present invention may be about 80%-100%, much greater than that of the current devices. In addition, 30 known negative samples have been tested using the device of the present invention, and it did not give any positive results, indicating that the device of the present invention does not adversely change the specificity for detecting an analyte in a liquid sample and, as well, the results for negative samples are not affected.

What is claimed is:

1. A device for determining the presence of an analyte in a liquid sample, the device comprising:
    a test strip defining a flow path, comprising:
        a second reagent zone positioned along the flow path, the second reagent zone comprising a first binding agent, the first binding agent being mobilizable by the liquid sample, the first binding agent being capable of binding the analyte to form a first complex;
        a first reagent zone located downstream of the second reagent zone along the flow path, the first reagent zone comprising a second binding agent, the second binding agent being mobilizable by the liquid sample, the second binding agent being capable of binding the first complex to form a second complex, the second binding agent comprising a detectable label; and
        a test zone located downstream of the first reagent zone along the flow path, the test zone comprising a third binding agent, the third binding agent being immobilized in the test zone, the third binding agent being capable of binding the first or second complex;
    wherein the second reagent zone is separable from the first reagent zone, and wherein prior to placing said second reagent zone in fluidic communication with the test strip, the liquid sample has been in contact with the second reagent zone for a period of time sufficient to effect formation of the first complex.

2. The device of claim 1, wherein the third binding agent is capable of binding the second complex via binding to the analyte when the analyte is bound to the first binding agent to form a third binding agent-analyte-first binding agent sandwich.

3. The device of claim 1, wherein the first binding agent comprises an antibody.

4. The device of claim 1, wherein the analyte comprises a drug abuse chemical.

5. The device of claim 4 wherein the drug of abuse chemical is THC or BZO.

6. The device of claim 1, wherein the detectable label is a color particle or a water-soluble dye.

7. The device of claim 1, wherein the second binding agent is capable of binding the first binding agent to form a second complex if analyte is not present in the sample, and wherein the third binding agent is capable of binding the first binding agent.

8. The device of claim 1, wherein at least a portion of the first binding agent is immobilized in the second reagent zone, and at least a portion of the first binding agent being mobilizable by the liquid sample, the first binding agent being capable of binding the analyte to form a first complex, and wherein the third binding agent is capable of binding the second complex.

* * * * *